(12) United States Patent
Okano et al.

(10) Patent No.: US 10,799,103 B2
(45) Date of Patent: Oct. 13, 2020

(54) ENDOSCOPE HAVING IMAGE ACQUISITION WINDOWS AND CORRESPONDING CLEANING NOZZLES ON FRONT AND CIRCUMFERENTIAL SURFACES

(71) Applicant: OLYMPUS CORPORATION, Tokyo (JP)

(72) Inventors: Hiromasa Okano, Ome (JP); Jin Ito, Tokyo (JP); Takanori Watanabe, Fuchu (JP); Kento Hashimoto, Hachioji (JP); Takeo Suzuki, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 346 days.

(21) Appl. No.: 15/819,498

(22) Filed: Nov. 21, 2017

(65) Prior Publication Data

US 2018/0084983 A1 Mar. 29, 2018

Related U.S. Application Data

(63) Continuation of application No. PCT/JP2016/063885, filed on May 10, 2016.

(30) Foreign Application Priority Data

May 25, 2015 (JP) ................................. 2015-105642

(51) Int. Cl.
*A61B 1/12* (2006.01)
*A61B 1/00* (2006.01)
(Continued)

(52) U.S. Cl.
CPC ............ *A61B 1/126* (2013.01); *A61B 1/0008* (2013.01); *A61B 1/008* (2013.01);
(Continued)

(58) Field of Classification Search
CPC .............. A61B 1/0008; A61B 1/00091; A61B 1/00177; A61B 1/0615; A61B 1/126;
(Continued)

(56) References Cited

U.S. PATENT DOCUMENTS 4,040,413 A * 8/1977 Ohshiro ............. A61B 1/00082
600/116
4,066,070 A * 1/1978 Utsugi ............... A61B 1/00082
600/115
(Continued)

FOREIGN PATENT DOCUMENTS

JP H08076023 A 3/1996
JP H11253401 A 9/1999
(Continued)

OTHER PUBLICATIONS

International Search Report dated Aug. 2, 2016 issued in PCT/JP2016/063885.

*Primary Examiner* — Aaron B Fairchild
(74) *Attorney, Agent, or Firm* — Scully, Scott, Murphy & Presser, P.C.

(57) ABSTRACT

An endoscope of the invention includes: an insertion portion; a distal end portion; a pair of first observation image acquiring sections; a second observation image acquiring section; a pair of nozzles, each of which includes a spouting port for spouting fluid toward each of the pair of first observation image acquiring sections; a pair of first protruding portions, each of which is located close to the front surface of the distal end portion and has a maximum dimension in the radial direction larger than a dimension in the radial direction of each of the nozzles, and a pair of second protruding portions, each of which is located farther from the front surface of the distal end portion and has a maximum dimension in the radial direction larger than the dimension in the radial direction of each of the nozzles.

8 Claims, 14 Drawing Sheets

(51) Int. Cl.
  *A61B 1/06* (2006.01)
  *A61B 1/008* (2006.01)
  *A61B 1/05* (2006.01)

(52) U.S. Cl.
  CPC ...... *A61B 1/00091* (2013.01); *A61B 1/00177* (2013.01); *A61B 1/00181* (2013.01); *A61B 1/05* (2013.01); *A61B 1/0615* (2013.01); *A61B 1/0684* (2013.01)

(58) Field of Classification Search
  CPC ... A61B 1/00174; A61B 1/00181; A61B 1/06; A61B 1/12; A61B 1/00082; A61B 1/00179; A61B 1/00125; A61B 1/00126
  See application file for complete search history.

(56) References Cited

U.S. PATENT DOCUMENTS

| | | | | |
|---|---|---|---|---|
| 4,224,929 | A | * | 9/1980 | Furihata ............. A61B 1/00082 600/107 |
| 5,569,162 | A | | 10/1996 | Komi |
| 2011/0282155 | A1 | * | 11/2011 | Kase .................... A61B 1/0615 600/165 |
| 2012/0232340 | A1 | * | 9/2012 | Levy ................... A61B 1/0008 600/104 |

FOREIGN PATENT DOCUMENTS

| | | | |
|---|---|---|---|
| JP | 2001286434 | A | 10/2001 |
| JP | 2013542467 | A | 11/2013 |
| JP | 2013544617 | A | 12/2013 |
| JP | 2014524819 | A | 9/2014 |

* cited by examiner

ENDOSCOPE HAVING IMAGE ACQUISITION WINDOWS AND CORRESPONDING CLEANING NOZZLES ON FRONT AND CIRCUMFERENTIAL SURFACES

CROSS REFERENCE TO RELATED APPLICATION

This application is a continuation application of PCT/JP2016/063885 filed on May 10, 2016 and claims benefit of Japanese Application No. 2015-105642 filed in Japan on May 25, 2015, the entire contents of which are incorporated herein by this reference.

BACKGROUND OF THE INVENTION

1. Field of the Invention

The present invention relates to an endoscope provided with an observation image acquiring section that is capable of observing a lateral field of view.

2. Description of the Related Art

Conventionally, endoscopes including an insertion portion formed in an elongated shape have been widely used in medical fields and industrial fields, for example. Among such endoscopes, a medical endoscope for use in the medical fields is configured to be capable of observing an organ in a body cavity by inserting an elongated insertion portion into the body cavity as a subject, and performing various kinds of treatment, as needed, by using a treatment instrument inserted in a treatment instrument insertion channel provided in the endoscope. In addition, an industrial endoscope for use in the industrial fields is configured to be capable of observing and examining a state in an object, for example, a flaw, corrosion, or the like, by inserting an elongated insertion portion into the inside of the object such as a jet engine, factory piping, and the like.

In recent years, various proposals have been disclosed for configurational devising for allowing examination and the like using a conventional endoscope to be performed more easily. For example, Japanese Unexamined Patent Application Publications Nos. 2013-544617, 2013-542467, and 2014-524819 disclose various endoscopes that is configured to acquire a front field-of-view image, with the front side of the insertion direction (longitudinal axis direction) of the endoscope insertion portion as an observation field of view, and also configured to simultaneously acquire lateral field-of-view images, with the lateral side of the endoscope insertion portion as an observation field of view.

The endoscopes disclosed in the Japanese Unexamined Patent Application Publications Nos. 2013-544617, 2013-542467, and 2014-524819 include a front observation optical system for acquiring a front field-of-view image, with the front side of the insertion direction (longitudinal axis direction) of the endoscope insertion portion as an observation field of view and a lateral observation optical system for acquiring lateral field-of-view images, with the lateral side of the endoscope insertion portion as an observation field of view. In the vicinity of the front observation optical system and the lateral observation optical system, nozzles, each of which includes a spouting port for spouting cleaning solution, gas, or the like for cleaning the outer surface of each of the optical systems, are respectively disposed so as to protrude toward the front side and the lateral side.

SUMMARY OF THE INVENTION

An endoscope according to one aspect of the present invention includes: an insertion portion to be inserted into an inside of a subject; a distal end portion disposed on a distal end side in a direction of a longitudinal axis of the insertion portion; a pair of first observation image acquiring sections provided on a circumferential surface around the longitudinal axis of the distal end portion, each of the pair of first observation image acquiring sections acquiring a first observation image from a first region of the subject; a second observation image acquiring section provided on a front surface of the distal end portion, the second observation image acquiring section acquiring a second observation image from a second region of the subject which is different from the first region; a pair of nozzles, each of which is provided so as to protrude from the circumferential surface of the distal end portion in a radial direction of the distal end portion and includes a spouting port configured to spout fluid in a direction along the longitudinal axis toward each of the pair of first observation image acquiring sections; a pair of first protruding portions, each of which is provided so as to protrude from the circumferential surface of the distal end portion in the radial direction of the distal end portion and located at a position closer to the front surface of the distal end portion with respect to the pair of first observation image acquiring sections and the pair of nozzles, a maximum dimension in the radial direction of each of the first protruding portions being larger than a dimension in the radial direction of each of the nozzles; and a pair of second protruding portions, each of which is provided so as to protrude from the circumferential surface of the distal end portion in the radial direction of the distal end portion and located at a position farther from the front surface of the distal end portion with respect to the pair of first observation image acquiring sections and the pair of nozzles, a maximum dimension in the radial direction of each of the second protruding portions being larger than the dimension in the radial direction of each of the nozzles.

DETAILED DESCRIPTION OF THE PREFERRED EMBODIMENT(S)

Figure 1:
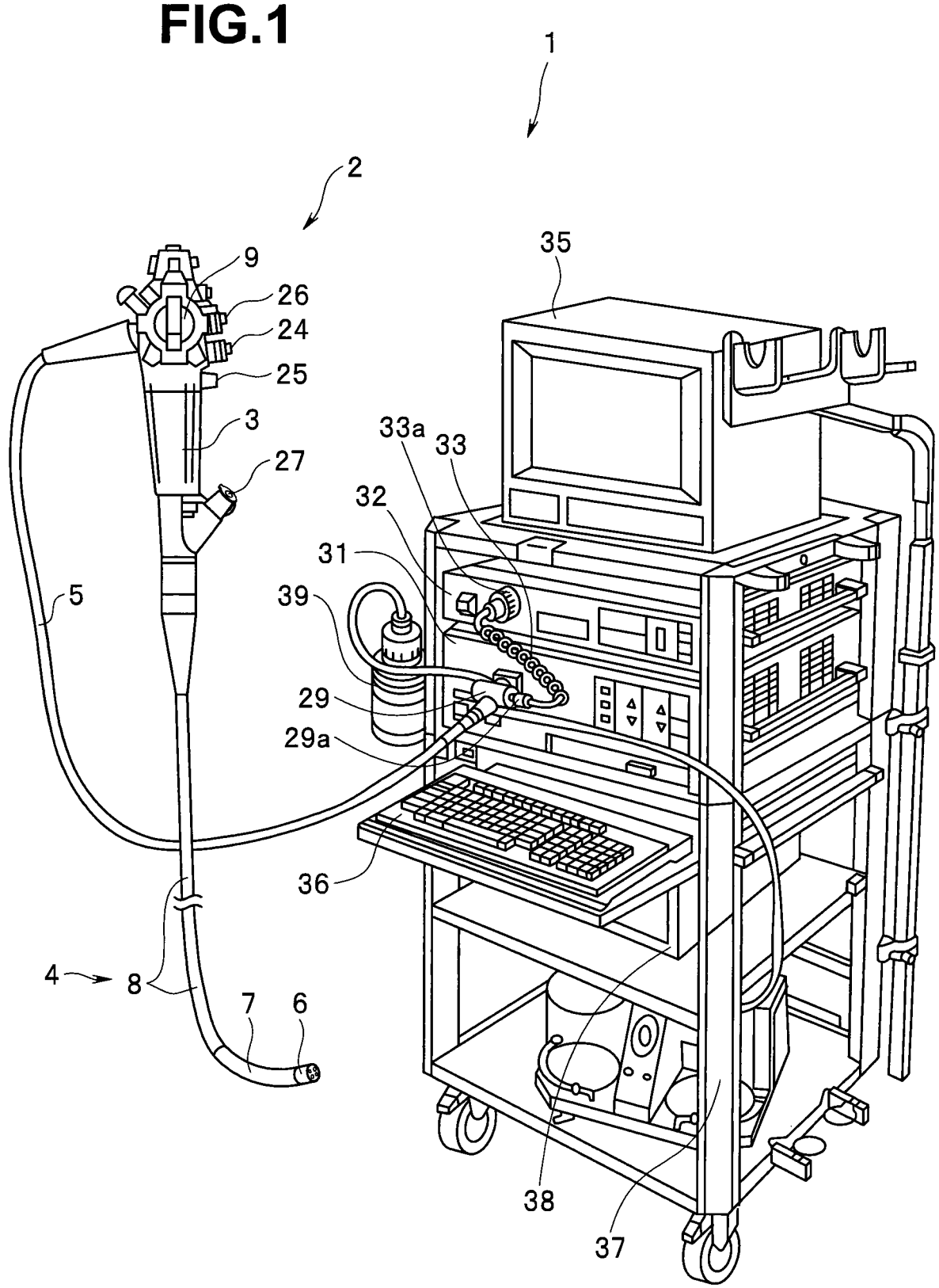
FIG. 1 is a schematic configuration view of an endoscope system including an endoscope according to a first embodiment of the present invention.

Hereinafter, the present invention will be described with embodiments shown in the drawings. The drawings to be used in the description below are schematic views, and there is a case where a different scale size or dimensional relationship is applied for each of constituent elements in order to allow the each of the constituent elements to be illustrated in a recognizable size on the drawings. Therefore, the present invention is not limited to the embodiments shown in the drawings with regard to the number, shapes, ratio of the sizes of the constituent elements, and a relative positional relationship among the constituent elements shown in these drawings.

First Embodiment

First, description will be made below on a schematic configuration of an entire endoscope system including an endoscope according to the first embodiment of the present invention, with reference to FIG. 1. FIG. 1 is a schematic configuration view of the endoscope system including the endoscope according to the first embodiment of the present invention.

An endoscope system 1 according to the present embodiment includes an endoscope 2, a light source apparatus 31, a video processor 32, a display apparatus 35, a key board 36 as an external input device, a stand 37, a recording apparatus 38, etc.

The endoscope 2 includes an operation portion 3, an insertion portion 4, a universal cord 5, etc. The insertion portion 4 is an elongated tubular-shaped constituent unit formed by including, in the following order from a distal end, a distal end portion 6, a bending portion 7, and a flexible tube portion 8. A proximal end of the insertion portion 4 is linked with a distal end of the operation portion 3. The insertion portion 4 is a constituent part to be inserted into a lumen, that is, a body cavity of a subject when the endoscope 2 is used.

The flexible tube portion 8 of the insertion portion 4 has flexibility and formed by using a hollow long tubular member, and a proximal end side of the flexible tube portion 8 is linked with a distal end of the operation portion 3 and a distal end side of the flexible tube portion 8 is linked with a proximal end of the bending portion 7. Inside the flexible tube portion 8, various signal lines, a light guide cable, a treatment instrument channel and the like, which are extended from the distal end portion 6, are inserted.

The bending portion 7 is a constituent part configured to be bendable in up/down directions and left/right directions with respect to an insertion axis of the insertion portion 4. As the configuration of the bending portion 7, a configuration in which a plurality of bending pieces are provided in a linked manner is applied, for example, similarly as the configuration applied to conventional common endoscopes. Therefore, description of detailed configuration and illustration of the internal configuration of the bending portion will be omitted. The proximal end side of the bending portion 7 is linked with the distal end of the flexible tube portion 8, and the distal end side of the bending portion 7 is linked with the proximal end of the distal end portion 6. Note that the bending portion 7 is configured to be bendable in the up/down directions and the left/right directions, for example, by operating a bending operation knob 9 of the operation portion 3, to be described later.

The distal end portion 6 is columnar-shaped constituent unit disposed at the distal-most side in the longitudinal axis direction (insertion axis direction; see the reference sign Ax in FIGS. 2 to 5 to be described later) of the insertion portion 4, made of a rigid member, including, at the distal end and inside thereof, various constituent members, and having a part which extends in the longitudinal axis direction of the insertion portion. The columnar shape includes a shape obtained by extending a shape, which is formed by cutting a part of a column or circle and including a cross section having a shape like a character "D", in a longitudinal direction, polygonal column shape, a shape obtained by removing a distal end portion of a cone, and the like. Note that the detailed configuration of the distal end portion 6 will be described later (see FIGS. 2 and 3).

The operation portion 3 is a constituent part grasped by a user with his or her hand when using the endoscope 2, for supporting the endoscope 2. A plurality of operation members for performing various kinds of operation are disposed on an outer circumferential surface of one end portion of the operation portion 3. The plurality of operation members are disposed respectively at portions within a range reached by the user's hand and fingers when the user grasps the operation portion 3. Specifically, the plurality of operation members include, for example, an air/liquid feeding operation button 24, a scope switch 25, a suction operation button 26, the bending operation knob 9, and the like.

The air/liquid feeding operation button 24 is an operation member for allowing gas, liquid, and the like for cleaning to be spouted selectively from a front field-of-view observation window nozzle 19 and lateral field-of-view observation window nozzles 22 (to be described later; see FIGS. 2 to 5) which are provided at the distal end portion 6 of the insertion portion 4.

The suction operation button 26 is an operation member for performing suction operation for collecting mucus and the like in the body cavity from a channel distal end opening portion (not shown) provided at the distal end portion 6 of the insertion portion 4.

The scope switch 25 is an operation member for switching a display mode when an endoscopic image acquired by an image pickup section (not shown; a constituent unit including an objective optical system, an image pickup device, etc.) which is provided at the distal end portion 6 of the insertion portion 4 is displayed using a display apparatus 35.

The respective operation members such as the air/liquid feeding operation button 24, the scope switch 25, and the suction operation button 26 operate in linkage with a plurality of operation switches corresponding to the respective operation members in the operation portion 3. The plurality of operation switches are mounted on an internal main substrate (not shown) of the operation portion 3. The internal main substrate of the operation portion 3 is electrically connected with the video processor 32. With such a configuration, when any of the operation members is operated by the user, a predetermined instruction signal corresponding to the operation is generated from the operation switch that operates in linkage with the operated operation member. The instruction signal is transmitted to the video processor 32, and control processing corresponding to the instruction signal is executed.

The bending operation knob 9 is a rotation operation member for operating a bending operation mechanism (not shown) disposed in the operation portion 3.

The operation members provided at the operation portion 3 include also various kinds of operation members other than the above-described examples. However, since the individual operation members are the same as those applied to the conventional common endoscopes, the detailed descriptions and illustrations thereof will be omitted.

In addition, at a portion close to the distal end of the operation portion 3, a treatment instrument insertion port 27 is formed so as to protrude outward from the lateral side. The treatment instrument insertion port 27 is communicated with a treatment instrument channel (not shown) inserted through the inside of the operation portion 3 and the insertion portion 4. The treatment instrument channel is made of a tubular member such as a tube which is disposed so as to be inserted through the operation portion 3 and the insertion portion 4 and which reaches a channel distal end opening portion (not shown) which opens on the front surface of the distal end portion 6 of the insertion portion 4.

When performing treatment or the like by using a treatment instrument, not shown, through the endoscope 2 of the endoscope system 1, the user inserts a predetermined treatment instrument from the treatment instrument insertion port 27, to cause the treatment instrument to pass through the inside of the treatment instrument channel, and thereafter causes the distal end part of the treatment instrument to protrude from the channel distal end opening portion toward the front side of the insertion direction. Such operation enables the distal end portion of the treatment instrument to reach a desired portion to be examined in the body cavity, thereby enabling various kinds of treatment such as medical attendance to be performed.

The universal cord 5 is extended outward from the side portion of the operation portion 3. The universal cord 5 is a cable member through which a plurality of signal lines, the light guide cable, an air/liquid feeding tube, a suction tube, and the like are inserted. The universal cord 5 includes at the distal end thereof a connector 29.

The connector 29 is provided with a fluid conduit connection pipe sleeve (not shown), a light guide pipe sleeve (not shown) as an illumination light supplying end portion, an electric contact portion 29a, and the like. An air/liquid feeding apparatus 39, the light source apparatus 31, and one end of a connection cable 33 are detachably connected to the fluid conduit connection pipe sleeve, the light guide pipe sleeve, and the electric contact portion 29a, respectively.

At the other end of the connection cable 33, a connector 33a is provided, and the connector 33a is connected to the video processor 32 which serves as signal processing means and control means.

The light source apparatus 31 is a constituent unit that generates illumination light. As described above, the light guide cable is connected to the light source apparatus 31. The light guide cable is inserted through the inside of the universal cord 5, and thereafter passed through the inside of the operation portion 3 and the insertion portion 4, to reach the inside of the distal end portion 6 of the insertion portion 4. With such a configuration, the illumination light emitted from the light source apparatus 31 is guided to the distal end portion 6 through the light guide cable.

The distal end side of the light guide cable is diverged at a predetermined portion inside the insertion portion 4, for example, though illustration thereof is omitted. The respective distal ends of the diverged parts of the light guide cable are disposed so as to be connected to predetermined portions (respective illumination windows 14, 15; see FIGS. 2 and 3) inside the distal end portion 6, with one of the diverged parts as a lateral field-of-view illumination light guide and the other of the diverged parts as a front field-of-view illumination light guide.

Specifically, the distal end of the lateral field-of-view illumination light guide is disposed in the vicinity of the lateral field-of-view illumination window 15 of the distal end portion 6. With such a configuration, the illumination light guided from the light source apparatus 31 to the lateral field-of-view illumination light guide is emitted outward from the lateral field-of-view illumination window 15 to illuminate the lateral field of view (see FIGS. 2 and 3).

In addition, the distal end of the front field-of-view illumination light guide is connected to the front field-of-view illumination window 14 provided on the distal end surface of the distal end portion 6. With such a configuration, the illumination light guided from the light source apparatus 31 to the front field-of-view illumination light guide is emitted outward from the front field-of-view illumination window 14 to illuminate the front field of view (see FIG. 2).

The video processor 32 is control means that integrally controls the endoscope system 1 and also signal processing means that processes various kinds of electric signals. The video processor 32 supplies a control signal for driving the image pickup section or the like, and receives the instruction signals from the various operation members of the operation portion 3 to output control signals corresponding to the instruction signals, for example. In addition, the video processor 32 receives an image signal outputted from (the image pickup device) of the image pickup section and performs predetermined signal processing on the received image signal, to generate an image signal for display and image data for recording, for example. The video processor 32 includes inside thereof an image processing section that receives various instruction signals to perform image signal processing corresponding to the various instructions on the output signal (image signal) from the image pickup section, and a plurality of substrate units that constitute an electronic control circuit such as an operation detection section that detects the instruction signals from the operation portion 3.

The display apparatus 35 is a constituent unit that receives the image signal for display generated by the video processor 32, to continuously display an endoscopic image on a display screen. Not only an LCD (liquid crystal display) apparatus and an OEL (organic electro-luminescence) display apparatus, but also a common display apparatus using a CRT (cathode ray tube (Braun tube)) is employed as the display apparatus 35, for example.

The key board 36 is an external input device electrically connected with the video processor 32, for inputting an instruction and various kinds of information such as patient information to the video processor 32. Note that, as the external input device connected with the video processor 32, not only the key board 36 but also a pointing device such as a mouse, a track ball, a joystick, and a touch pad, a foot switch, and in addition, existing various devices such as a voice input apparatus, a touch panel disposed on the display screen of the display apparatus 35 can be applied as needed. The number of external input device is not limited to one, and a plurality of external input devices may be provided at the same time.

The stand 37 is a storage and installation apparatus on which the constituent units such as the light source apparatus 31, the video processor 32, the display apparatus 35, the external input device (key board 36, etc.) are placed, and on which the endoscope 2 which is not in use is temporarily placed in a suspended manner, for example.

The recording apparatus 38 is a constituent part for recording the acquired endoscopic image data, and various associated data such as patient data.

The entire schematic configuration of the endoscope system 1 according to the present embodiment is as described above. The configurations omitted in the above description are the same as those in the common endoscope systems which have been put into practical use.

Next, the configuration of the distal end portion 6 will be described below, with reference mainly to FIGS. 2 and 3.

Figure 2:
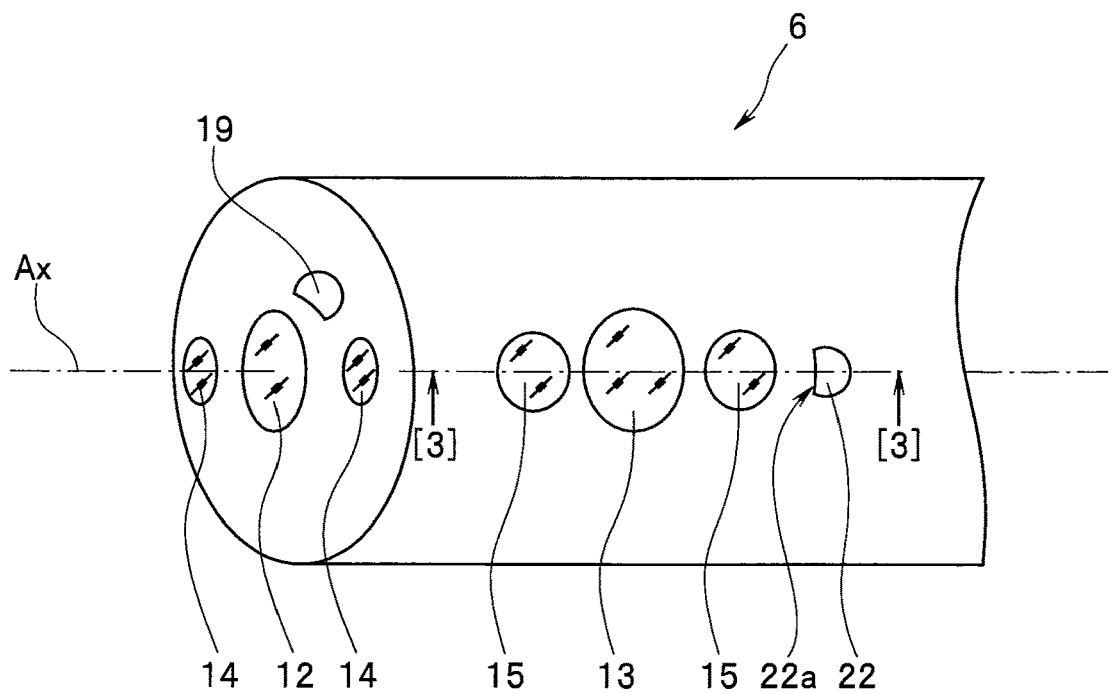
FIG. 2 is a main-part enlarged schematic configuration view showing a schematic configuration of a distal end portion of the endoscope according to the first embodiment of the present invention.

FIG. 2 is a main-part enlarged schematic configuration view showing the distal end portion 6 of the endoscope 2 according to the present embodiment in an enlarged manner to describe the schematic configuration of the distal end portion 6. FIG. 3 is a main-part enlarged cross-sectional view taken along the line [3]-[3] in FIG. 2. FIG. 4 is a main-part enlarged schematic configuration view mainly illustrating the side surface of the distal end portion 6 of the endoscope 2 according to the present embodiment. FIG. 5 is a conceptual view showing an appearance of a vicinity of the distal end portion 6 when the endoscope 2 according to the present embodiment is inserted into a body cavity of a subject.

Figure 3:
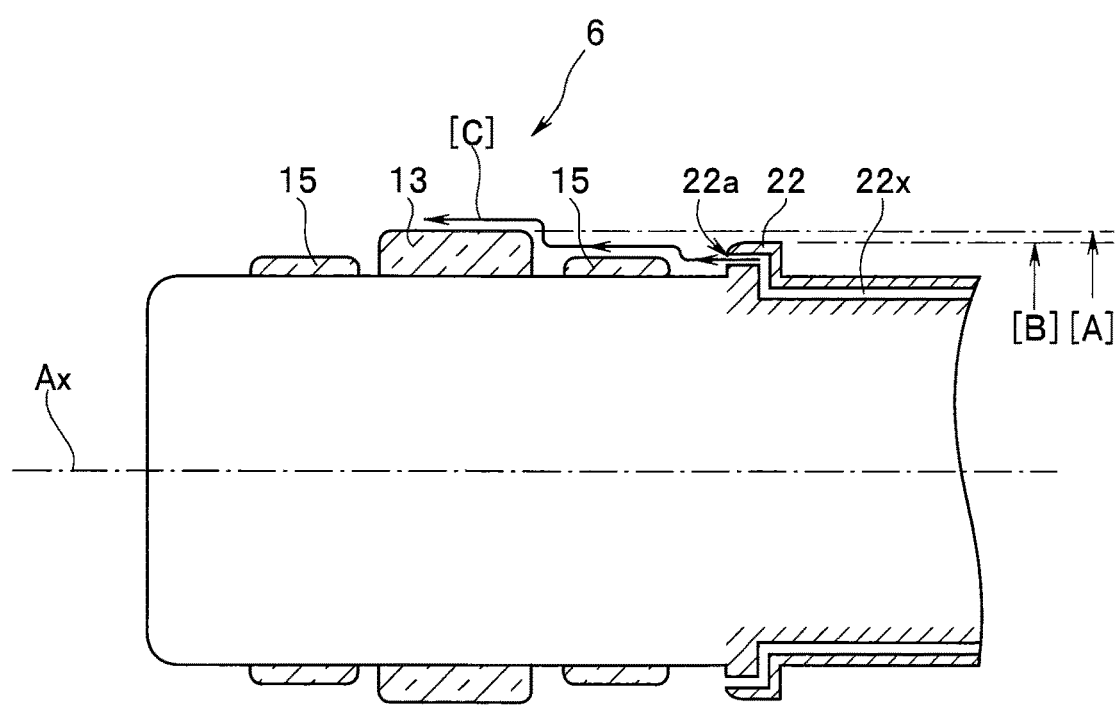
FIG. 3 is a main-part enlarged cross-sectional view taken along the line [3]-[3] in FIG. 2.
Figure 4:
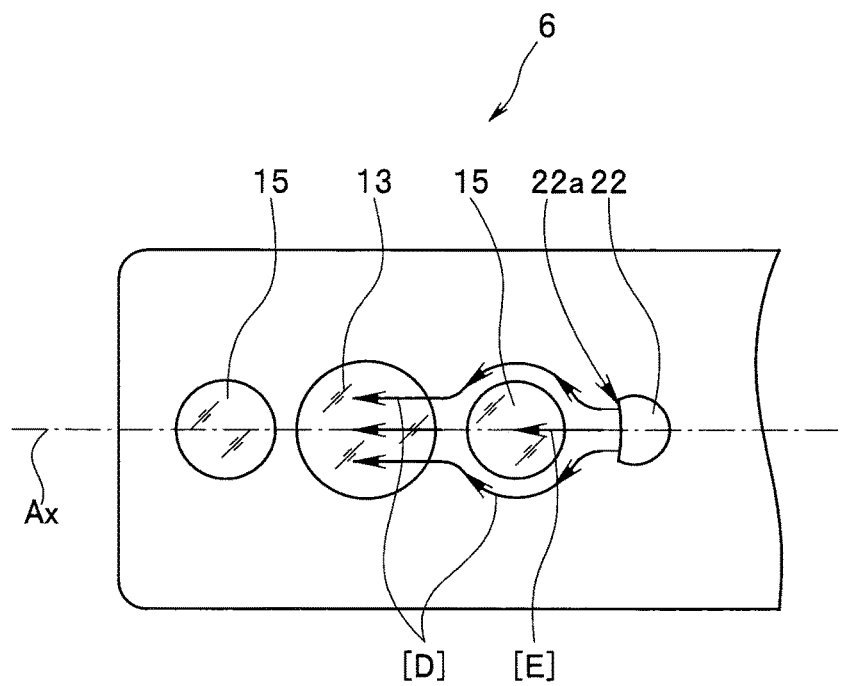
FIG. 4 is a main-part enlarged schematic configuration view mainly illustrating a side surface of the distal end portion of the endoscope according to the first embodiment of the present invention.
Figure 5:
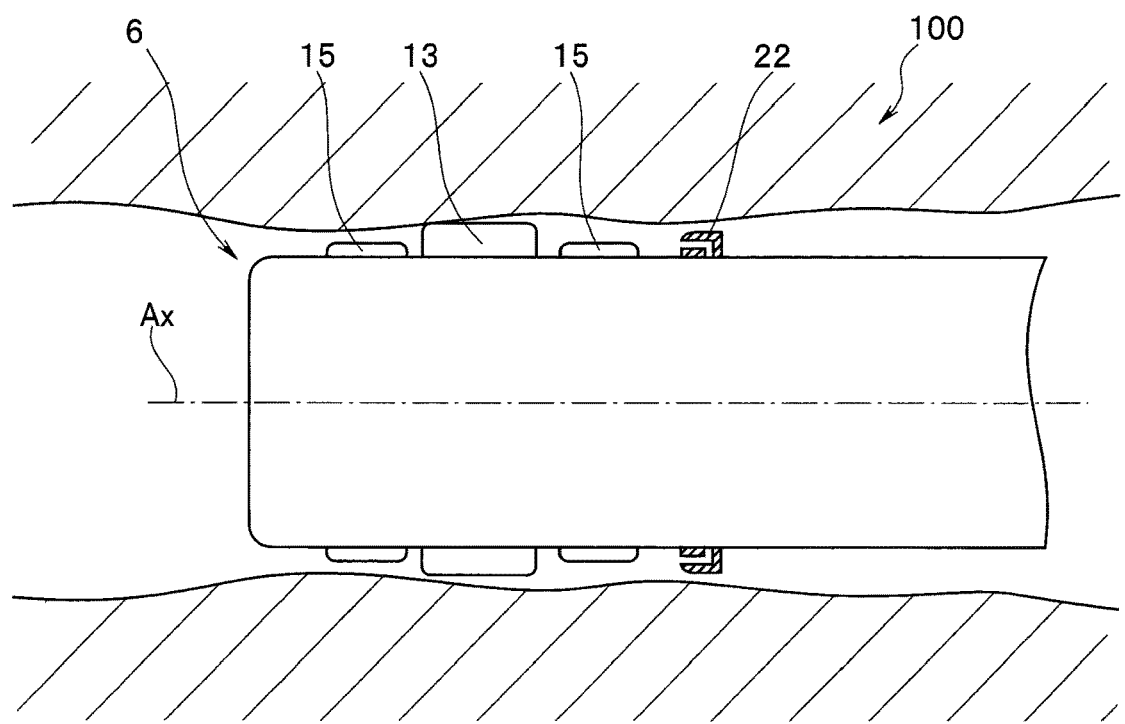
FIG. 5 is a conceptual view showing an appearance of a vicinity of the distal end portion when the endoscope according to the first embodiment of the present invention is inserted into a body cavity of a subject.

Note that FIGS. 2 to 5 mainly illustrate only the constituent parts serving as the gist of the present invention, and illustrations of other constituent members are omitted. In addition, in FIGS. 3 to 5, only the constituent members arranged on the circumferential surface around the longitudinal axis (that is, the lateral side) of the distal end portion are illustrated, and illustrations of the constituent elements on the front surface of the distal end portion are omitted. Furthermore, FIG. 3 shows the longitudinal cross section along the longitudinal axis of the endoscope, and omits the illustration of the detailed configuration inside the distal end portion 6, since the configuration inside the distal end portion 6 is not directly related to the present invention. Furthermore, FIG. 5 illustrates the distal end portion, with only the nozzles 22 being partially shown as cross sections. Note that the reference sign Ax shows the longitudinal axis (also referred to as insertion axis) of the endoscope 2 in FIGS. 2 to 5.

The distal end portion 6 of the endoscope 2 according to the present embodiment includes on the front surface thereof a plurality of front field-of-view illumination windows 14, one front field-of-view observation window 12, one front field-of-view observation nozzle 19, and the like. In addition, in the circumferential direction around the longitudinal axis Ax of the distal end portion 6, that is, on the outer circumferential surface of the distal end portion 6, a plurality of lateral field-of-view illumination windows 15, a plurality of lateral field-of-view observation windows 13, a plurality of lateral field-of-view observation window nozzles 22, and the like are disposed.

Note that, in the endoscope 2 of the present embodiment, a predetermined direction facing the lateral field of view is referred to as a first direction, and a predetermined field-of-view region including the first direction is referred to as a first region. The lateral field-of-view observation window 13 is a constituent part that constitutes a part of an observation image acquiring section for acquiring a lateral field-of-view image (first observation image) to be obtained from the lateral side as the first direction. That is, the first observation image is an observation image in the first direction which is a direction intersecting with the longitudinal axis Ax of the insertion portion 4 such as the direction substantially perpendicular to the longitudinal axis Ax, and which includes the lateral side (first region) of the insertion portion 4. Note that the observation image acquiring section includes a first image pickup section (not shown) that photoelectrically converts the lateral field-of-view image (first observation image).

In addition, in the endoscope 2 of the present embodiment, the direction facing the front field of view is referred to as a second direction which is different from the first direction (direction facing the lateral field of view), and the field-of-view region in the second direction is referred to as a second region including another region different from the first region.

The front field-of-view observation window 12 is a constituent part that constitutes a part of a second observation image acquiring section for acquiring a front field-of-view image (referred to as a second observation image as another observation image including a part different from the first observation image) to be obtained from the front side as the second direction. That is, the second observation image is an observation image in the second direction which is substantially parallel to the longitudinal direction of the insertion portion 4 and which includes the front side of the insertion portion 4. Note that the second observation image acquiring section includes a second image pickup section (not shown) which photoelectrically converts the front field-of-view image (second observation image) and which is different from the first image pickup section.

In other words, the front field-of-view observation window 12 (second observation image acquiring section) is provided at the distal end portion 6 in the direction along the longitudinal axis Ax of the insertion portion 4, and acquires the second observation image (front field-of-view image) from the second region of a subject, at least a part of which is different from the first region.

That is, the front field-of-view observation window 12 is an opening window provided on the front surface of the distal end portion 6 for observing the front field of view. Furthermore, the front-field-of-view observation window 12 is a front observation optical system and is a front observation image acquiring section (second observation image acquiring section). In addition, an objective optical system, not shown, is fixedly disposed at the rear of the front field-of-view observation window 12 inside the distal end portion 6, though illustration thereof is omitted. The front field-of-view observation window 12 is an opening that receives a light flux incident from the front side in the insertion direction of the endoscope 2 to guide the received light flux to the objective optical system (not shown). Note that an image pickup section (not shown) that photoelectrically converts the observation image acquired by the observation image acquiring section is disposed at the rear portion on the optical axis of the objective optical system.

The front field-of-view observation window nozzle 19 is a constituent part formed by including a spouting port for spouting a fluid such as cleaning solution or gas (hereinafter, referred to as cleaning solution or the like) for cleaning an outer surface of the front field-of-view observation window 12.

The front field-of-view illumination window 14 is an opening window for illumination that emits the illumination light to the subject as the observation target in the front field of view. To this end, the distal end surface of the front field-of-view illumination light guide (not shown) diverged from the light guide cable (not shown) is disposed so as to be opposed to the rear side of the front field-of-view illumination window 14 in the distal end portion 6, though illustration thereof is omitted. With such a configuration, the illumination light guided from the light source apparatus 31 to the front field-of-view illumination light guide (not shown) is guided to the front field-of-view illumination window 14, to be emitted outward to the front side from the front field-of-view illumination window 14 and illuminates the front field of view. Note that, in the present embodiment, an example is shown in which the two front field-of-view illumination windows 14, as one pair, are disposed at positions opposed to each other across the front field-of-view observation window 12.

On the other hand, the lateral field-of-view observation window 13 is a (lateral) observation image acquiring section provided for observing the lateral field-of-view image (first observation image) in the lateral field of view (first region) in the body cavity of the subject. The lateral field-of-view observation window 13 is provided in plurality as a plurality of opening windows provided on the circumferential surface of the distal end portion 6, and is a lateral observation optical system.

In the present embodiment, an example in which a pair of lateral field-of-view observation windows 13 are provided at positions so as to separate from each other around the longitudinal axis Ax by the angle of 180 degrees on the circumferential surface (circumferential direction) of the distal end portion 6. In the internal space of the distal end portion 6, which faces the lateral field-of-view observation windows 13, an objective optical system including a reflective optical system is fixedly disposed. That is, the lateral field-of-view observation windows 13 are openings for receiving the light fluxes incident from the both lateral sides across the longitudinal axis Ax of the distal end portion 6, to guide the light fluxes to the objective optical system. Note that only one of the pair of lateral field-of-view observation windows 13 is shown in FIG. 3, and the other is provided at the position not illustrated in the drawing.

The lateral field-of-view illumination window 15 is an opening window as an illumination portion that emits the illumination light toward the subject as the observation target in the lateral field of view. To this end, the lateral field-of-view illumination window 15 is provided as the illumination portion provided in a direction perpendicular to the longitudinal axis Ax of the endoscope 2, that is, provided on the circumferential surface of the distal end portion 6 at a portion different from the portion where the lateral field-of-view observation window 13 (observation image acquiring section) is provided, and open in the radial direction (that is, lateral side of the distal end portion 6) for illuminating the first region of the subject. One pair of lateral field-of-view illumination windows 15 are provided for each of the pair of the lateral field-of-view observation windows 13. That is, the one pair of lateral field-of-view illumination windows 15 are arranged at positions so as to be opposed to each other across the corresponding one of the pair of lateral field-of-view observation windows 13.

Note that the distal end surface of the lateral field-of-view illumination light guide (not shown) diverged from the light guide cable (not shown) is arranged so as to be opposed to the rear side of the lateral field-of-view illumination window 15 in the distal end portion 6, though the illustration thereof is omitted. With such a configuration, the illumination light guided from the light source apparatus 31 to the lateral field-of-view illumination light guide (not shown) is guided to the lateral field-of-view illumination window 15, and emitted outward to the lateral side, to illuminate the lateral field of view.

The lateral field-of-view observation window nozzle 22 is a constituent part formed by including a spouting port 22a for spouting cleaning solution or the like to the outer surface of the lateral field-of-view observation window 13, in order to clean the outer surface of the lateral field-of-view observation window 13. The lateral field-of-view observation window nozzle 22 is provided for each of the pair of lateral field-of-view observation windows 13 so as correspond one to one to the each of the pair of lateral field-of-view observation windows 13. The lateral field-of-view observation window nozzle 22 is arranged at a portion close to the proximal end of the distal end portion 6. The spouting port 22a of the lateral field-of-view observation window nozzle 22 is open toward the distal end side of the distal end portion 6 in the direction along the longitudinal axis Ax. The width dimension of the spouting port 22a is set so as to be narrower than the width dimension of the lateral field-of-view observation window 13, for example.

The lateral field-of-view observation window nozzle 22 is connected with the distal end of the air/liquid feeding tube (the reference sign 22x in FIG. 3) inside the distal end portion 6, and the air/liquid feeding tube 22x is passed through the inside of the insertion portion 4, then passed through the operation portion 3 and the universal cord 5, and thereafter connected to the air/liquid feeding apparatus 39, through a fluid conduit connection pipe sleeve (not shown) of the connector 29. With such a configuration, when the air/liquid feeding apparatus 39 is controlled based on the instruction signal from the operation member such as the air/liquid feeding operation button 24 under the control by the video processor 32 and air/water feeding operation is performed, the cleaning solution or the like is spouted from the spouting port 22a of the lateral field-of-view observation window nozzle 22 at a predetermined timing.

Note that, in the present embodiment, one of the pair of lateral field-of-view illumination windows 15, the lateral field-of-view observation window 13, the other of the pair of lateral field-of-view illumination windows 15, and the lateral field-of-view observation window nozzle 22 are arranged on the circumferential surface of the distal end portion 6 so as to align in the above-described order from the distal end side in the direction along the longitudinal axis Ax.

Furthermore, at the distal end portion 6 of the endoscope 2 according to the present embodiment, the protruding position of the lateral field-of-view observation window nozzle 22 (see the reference sign [B] shown in FIG. 3) in the radial direction is formed so as to be lower than the protruding position of the lateral field-of-view observation windows 13 in the radial direction.

In other words, at the distal end portion 6, the maximum outer diameter (the reference sign [A]) of the portion where the lateral field-of-view observation windows 13 are protruded in the radial direction is set to be "larger" than the maximum outer diameter (the reference sign [B]) of the portion where the lateral field-of-view observation window nozzles 22 are protruded in the radial direction.

That is, at the distal end portion 6 including the lateral field-of-view observation window 13 (observation image acquiring section), the maximum protruding dimension of the lateral field-of-view observation window nozzle 22 in the radial direction is set to be shorter than the maximum protruding dimension of the lateral field-of-view observation window 13 (observation image acquiring section) in the radial direction around the longitudinal axis Ax. Note that the spouting port 22a is provided at a portion of the lateral field-of-view observation window nozzle 22.

In such a configuration, the cleaning solution or the like spouted from the spouting port 22a of the lateral field-of-view observation window nozzle 22 reaches the outer surface of the lateral field-of-view observation window 13 without any difficulty, as shown by the arrow [C] in FIG. 3 and the arrows [D], [E] in FIG. 4, to thereby be capable of cleaning the outer surface of the lateral field-of-view observation window 13.

Note that the maximum outer diameters of the protruding portions of the lateral field-of-view illumination windows 15 are set to be "smaller" than the maximum outer diameter (see the reference sign [B]) of the protruding portion of the lateral field-of-view observation window nozzles 22 (see FIG. 3, etc.) in the present embodiment. In such a configuration, the maximum outer diameters of the protruding portions of the lateral field-of-view illumination windows 15 have to be set in view of the following point. That is, at least the maximum outer diameter of the protruding portion of the proximal-end-side lateral field-of-view illumination windows 15 is set such that the illumination light emitted from each of the proximal-end-side lateral field-of-view illumination windows 15 is not shielded by each of the lateral field-of-view observation window nozzles 22. In such a setting, the maximum outer diameters of the protruding portions of the lateral field-of-view illumination windows 15 may be set to be "smaller" than the maximum outer diameter (reference sign [B]) of the protruding portion of the lateral field-of-view observation window nozzles 22.

The setting of the maximum outer diameters is not limited to the above-described setting. For example, the maximum outer diameters of the protruding portions of the lateral field-of-view illumination windows 15 may be set to be "larger" than the maximum outer diameter (reference sign [B]) of the protruding portion of the lateral field-of-view observation window nozzles 22.

That is, the maximum outer diameter (reference sign [B]) of the protruding portion of the lateral field-of-view observation window nozzles 22 has only to be set to be "smaller" than the maximum outer diameter of the protruding portion of the lateral field-of-view observation windows 13 or the respective maximum outer diameters of the protruding portions of the lateral field-of-view illumination windows 15.

Note that when the maximum outer diameter of protruding portion of the lateral field-of-view observation windows 13 is set to be the "largest", there is an advantage that the field of view of the lateral observation image can be effectively ensured.

In the endoscope 2 according to the present embodiment thus configured, in the situation shown in FIG. 5, that is, when the insertion/extraction operation or bending operation of the endoscope 2 is performed in the body cavity of the subject, among the plurality of constituent members (13, 15, 22, etc.) provided in a protruded manner on the lateral side (radial direction) of the distal end portion 6, the lateral field-of-view observation window nozzles 22, which possibly interfere with the insertion/extraction or bending operation of the endoscope 2 when coming into contact with the mucosa 100 on the inner wall of the body cavity, are always located at the positions where the lateral field-of-view observation window nozzles 22 hardly come into contact with the mucosa 100 on the inner wall of the body cavity. Therefore, such a configuration enables the insertion/extraction operation and the bending operation of the endoscope 2 to be always performed smoothly.

As described above, according to the first embodiment, the maximum outer diameter (reference sign [B]) of the protruding portion of the lateral field-of-view observation window nozzles 22 is set to be "smaller" than the maximum outer diameter (reference sign [A]) of the protruding portion of the lateral field-of-view observation windows 13 or the respective maximum outer diameters of the protruding portions of the lateral field-of-view illumination windows 15, thereby preventing the lateral field-of-view observation window nozzles 22 from contacting the mucosa on the inner wall of the body cavity when the insertion/extraction operation or the bending operation of the endoscope 2 is performed in the body cavity of the subject. As a result, the insertion/extraction operation and the bending operation of the endoscope 2 can be always performed smoothly.

Note that, in the above-described first embodiment, the position setting of the lateral field-of-view observation window nozzles 22 in the radial direction of the distal end portion 6 is performed by focusing on the maximum outer diameter of the protruding portion of the lateral field-of-view observation nozzles 22. However, the position setting may be performed by focusing on the positions of the spouting ports 22a. Such an exemplary configuration can be similarly applied to each of the embodiments to be described below.

That is, in the configuration of the above-described first embodiment, the maximum outer diameter (reference sign [A]) of the protruding portion of the lateral field-of-view observation windows 13 is set to be "larger" than the maximum outer diameter (reference sign [B]) of the protruding portion of the lateral field-of-view observation window nozzles 22, for example. However, the portion where the spouting ports 22a of the lateral field-of-view observation window nozzles 22 are disposed may be set as the maximum outer diameter, and the maximum outer diameter (reference sign [A]) of the protruding portion of the lateral field-of-view observation windows 13 may be set to be "larger" than the maximum outer diameter of the portion where the spouting ports 22a are disposed.

In addition, the above-described first embodiment shows the exemplary configuration in which the light guide for illumination is used as a configuration for guiding the illumination light to the respective illumination windows (14, 15). However, the present invention is not limited to the configuration, and a light-emitting member for illumination such as a light-emitting diode (LED) may be arranged at the rear portions of the respective illumination windows (14, 15), that is, inside the distal end portion 6, for example. The exemplary configuration can be similarly applied to each of the embodiments to be described later.

Furthermore, in the above-described first embodiment, the lateral field-of-view observation window nozzle 22 is arranged at the most proximal end side among the respective constituent members provided in a protruded manner on the circumferential surface of the distal end portion 6. However, the present invention is not limited to the configuration. For example, the lateral field-of-view observation window nozzle 22 may be provided on the distal end portion 6 at a portion close to the distal end. In that case, the spouting port 22a is disposed so as to open toward the proximal end side. Then, one pair of lateral field-of-view illumination windows 15 and the lateral field-of-view observation window 13 may be appropriately disposed on the proximal end side with respect to the lateral field-of-view observation window nozzle 22.

However, the arrangement space for the air/liquid feeding tube 22x to be connected to each of the lateral field-of-view observation window nozzles 22 has to be ensured inside the distal end portion 6. That is, arranging each of the lateral field-of-view observation window nozzles 22 at the portion close to the distal end side may result in a tendency for an increase in the diameter of the distal end portion 6. Therefore, in view of the internal configuration layout for preventing the increase in the diameter of the distal end portion 6, each of the lateral field-of-view observation window nozzles 22 is preferably disposed at the portion closer to the proximal end with respect to other constituent members such as the pair of lateral field-of-view illumination windows 15, the lateral field-of-view observation window 13, etc.

Second Embodiment

As described above, in the first embodiment, three kinds of constituent members, that is, the pair of lateral field-of-view illumination windows 15, the lateral field-of-view observation window 13, and the lateral field-of-view observation window nozzle 22 among the constituent members provided on the circumferential surface of the distal end portion 6 of the insertion portion 4 of the endoscope 2 are arranged so as to align in the direction of the longitudinal axis Ax (insertion axis).

That is, in this case, one of the pair of lateral field-of-view illumination windows 15 (the proximal-end-side lateral field-of-view illumination window 15) is arranged between the lateral field-of-view observation window 13 and the lateral field-of-view observation window nozzle 22.

In such an arrangement, part of the cleaning solution or the like spouted from the spouting port 22a of the lateral field-of-view observation window nozzle 22 passes over the outer surface of the proximal-end-side lateral field-of-view illumination window 15, and thereafter reaches the lateral field-of-view observation window 13.

Therefore, as a configuration in which devising is applied to allow the cleaning solution or the like spouted from the spouting port 22a of the lateral field-of-view observation window nozzle 22 to be directly applied to the outer surface of the lateral field-of-view observation window 13, description will be made below on a configuration of a distal end portion of an insertion portion of an endoscope according to the second embodiment.

Figure 6:
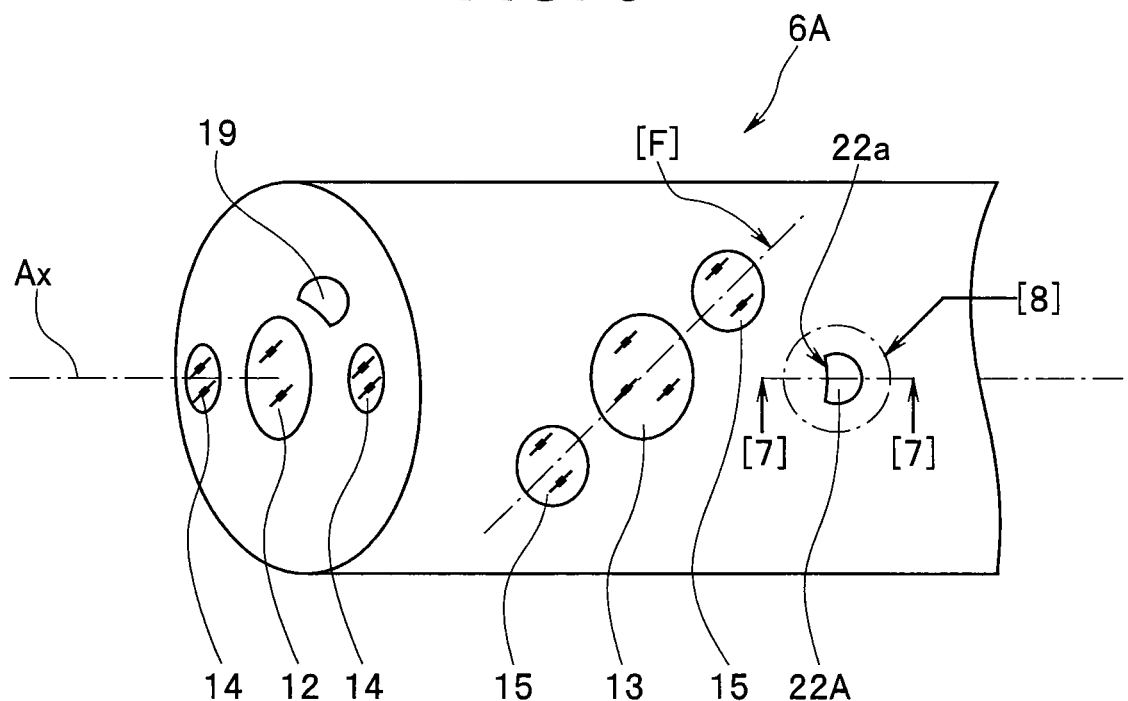
FIG. 6 is a main-part enlarged schematic configuration view of a distal end portion of an insertion portion of an endoscope according to a second embodiment of the present invention.

FIG. 6 is a main-part enlarged schematic configuration view of the distal end portion of the insertion portion of the endoscope according to the second embodiment of the present invention.

In the endoscope according to the present embodiment, among the constituent members provided on the circumferential surface of the distal end portion 6A, the lateral field-of-view observation window 13 and a lateral field-of-view observation window nozzle 22A are arranged so as to align in the direction along the longitudinal axis Ax. Furthermore, a pair of lateral field-of-view illumination windows 15 are arranged at positions opposed to each other, with the lateral field-of-view observation window 13 sandwiched therebetween. In this case, in the exemplary configuration of the present embodiment, the pair of lateral field-of-view illumination windows 15 and the lateral field-of-view observation window 13 are arranged so as to align on a line (see the reference sign [F] in FIG. 6) connecting the pair of lateral field-of-view illuminations windows 15 and the lateral field-of-view observation window 13. In this configuration, the line denoted by the reference sign [F] is a linear line inclined with respect to the longitudinal axis Ax.

Similarly as in the above-described first embodiment, at the distal end portion 6 including the lateral field-of-view observation window 13 (observation image acquiring section), the maximum protruding dimension of the lateral field-of-view observation window nozzle 22 in the radial direction is set so as to be shorter than the maximum protruding dimension of the lateral field-of-view observation window 13 (observation image acquiring section) in the radial direction around the longitudinal axis Ax or shorter than the maximum protruding dimensions of the lateral field-of-view illumination windows 15 in the radial direction around the longitudinal axis Ax.

With such a configuration, another constituent element such as one of the pair of lateral field-of-view illumination windows 15, that is, the proximal-end-side lateral field-of-view illumination window 15, is not arranged between the lateral field-of-view observation window 13 and the lateral field-of-view observation window nozzle 22. As a result, the cleaning solution or the like spouted from the spouting port 22a can directly reach the outer surface of the lateral field-of-view observation window 13.

Third Embodiment

Figure 7:
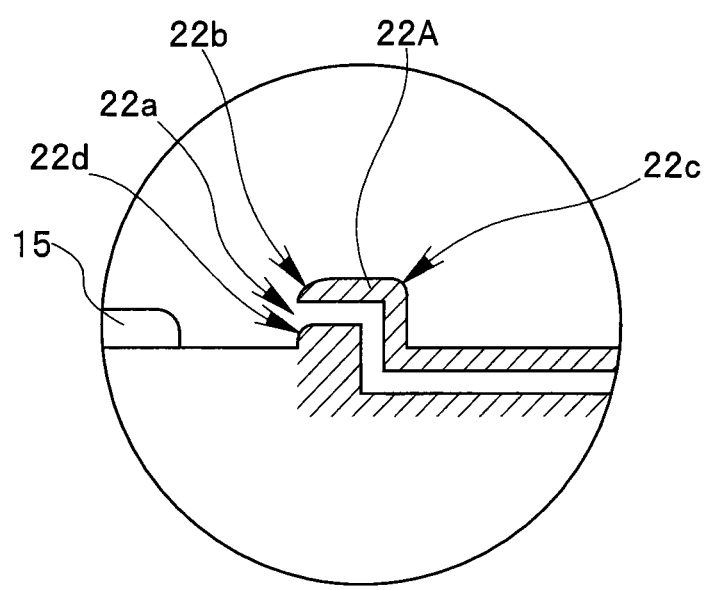
FIG. 7 illustrates a lateral field-of-view observation window nozzle provided at a distal end portion of an endoscope according to a third embodiment of the present invention, and is a main-part enlarged cross-sectional view of a portion corresponding to a part which is along the line [7]-[7] in FIG. 6.
Figure 8:
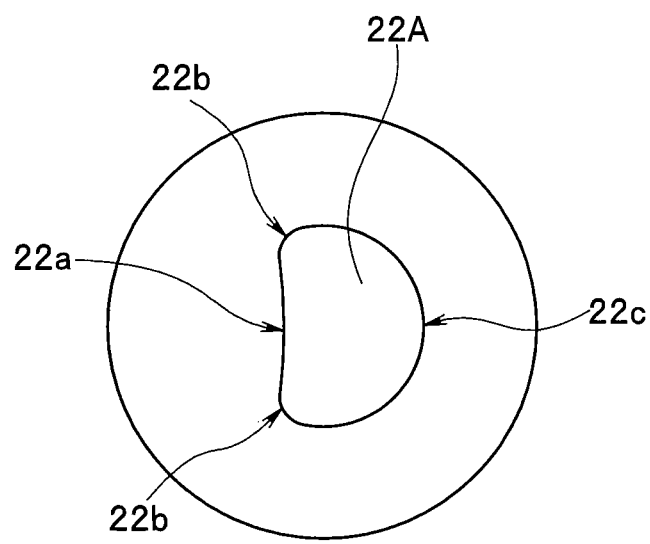
FIG. 8 is an enlarged plan view of a portion (lateral field-of-view observation window nozzle) shown with the reference sign [8] in FIG. 6 of the lateral field-of-view observation window nozzle in FIG. 7.

Furthermore, the third embodiment as shown in FIGS. 7 and 8 can be considered in which the embodiment shown in FIG. 6 is devised for enabling the insertion/extraction operation and the bending operation of the endoscope 2 to be more smoothly performed.

FIG. 7 illustrates a lateral field-of-view observation window nozzle provided at a distal end portion of an endoscope according to the third embodiment of the present invention. FIG. 7 is a main-part enlarged cross-sectional view of a portion corresponding to a part which is along the line [7]-[7] in FIG. 6. FIG. 7 mainly illustrates the cross section of the lateral field-of-view observation window nozzle in the endoscope according to the present embodiment by taking out the vicinity of the lateral field-of-view observation window nozzle. FIG. 8 is an enlarged plan view of a portion (lateral field-of-view observation window nozzle) shown with the reference sign [8] in FIG. 6.

As shown in FIGS. 7 and 8, the present embodiment shows an example in which round chamfering is applied to respective edge portions (22b, 22c, and 22d) on the outer surface of the lateral field-of-view observation window nozzle 22A. The predetermined surface processing is thus applied to the outer surface of the lateral field-of-view observation window nozzle 22A, thereby forming a smoother outer surface.

Therefore, with such processing, among the constituent members provided on the circumferential surface of the distal end portion 6 so as to protrude in the radial direction, the edge portions on the outer surface of the lateral field-of-view observation window nozzle 22A, which possibly interferes with the insertion/extraction operation and the bending operation of the endoscope 2 when coming into contact with the mucosa on the inner wall of the body cavity, are removed to form a smooth surface shape. Therefore, even if the lateral field-of-view observation window nozzle 22A contacts the mucosa on the inner wall of the body cavity, the lateral field-of-view observation window nozzle 22A can be slid smoothly on the surface of the mucosa. As a result, smoother insertion/extraction operation or bending operation of the endoscope 2 can be performed in the body cavity.

Fourth Embodiment

Figure 9:
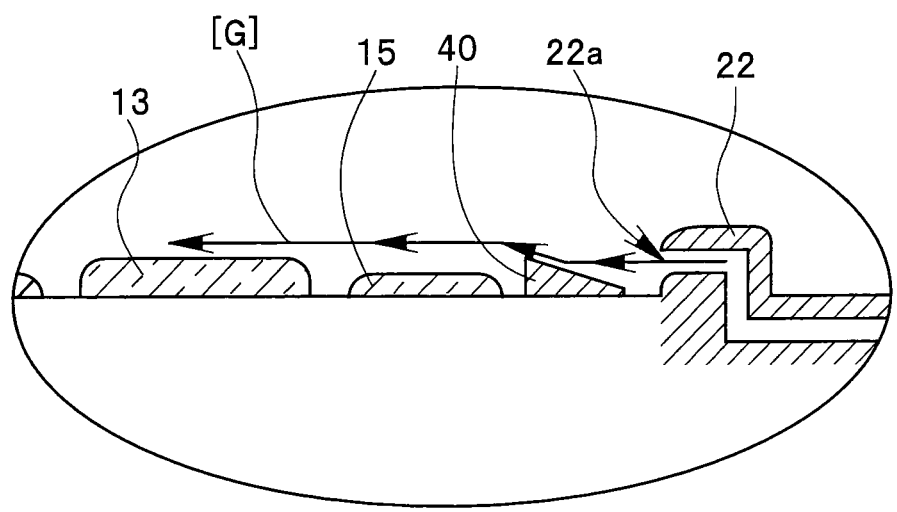
FIG. 9 is a main-part enlarged cross-sectional view illustrating, in an enlarged manner, a vicinity of a lateral field-of-view observation window nozzle at a distal end portion of an insertion portion of an endoscope according to a fourth embodiment of the present invention.

FIG. 9 is a main-part enlarged cross-sectional view illustrating, in an enlarged manner, a vicinity of a lateral field-of-view observation window nozzle at a distal end portion of an insertion portion of an endoscope according to the fourth embodiment of the present invention.

The present embodiment is an exemplary configuration in which the distal end portion 6 of the insertion portion of the endoscope according to the first embodiment is devised for enabling the cleaning solution or the like spouted from the spouting port 22a to smoothly and surely reach the lateral field-of-view observation window 13.

That is, at the distal end portion 6 of the insertion portion 4 of the endoscope 2 according to the first embodiment, the constituent members (15, 13, 22) provided on the circumferential surface of the distal end portion are arranged so as to align along the longitudinal axis Ax.

In contrast to the configuration, in the present embodiment, a flow adjusting portion 40 for adjusting the spouting route of the cleaning solution or the like spouted from the spouting port 22a is further provided at a portion which is between the lateral field-of-view observation window nozzle 22 and the proximal-end-side lateral field-of-view illumination window 15 of the pair of lateral field-of-view illumination windows 15 and which is in the vicinity of the spouting port 22a, as shown in FIG. 9.

The flow adjusting portion 40 is a member configured by including an inclined surface portion at a portion opposed to the opening of the spouting port 22a. The inclined surface portion of the flow adjusting portion 40 is formed so as to oppose to the opening of the spouting port 22a (see FIG. 9). The maximum protruding dimension of the top portion (the maximum protruding portion) of the inclined surface of the flow adjusting portion 40 is set to be "larger" than the maximum protruding dimension of the proximal-end-side lateral field-of-view illumination window 15 in the radial direction and to be substantially equal to or slightly "larger" than the maximum protruding dimension of the lateral field-of-view observation window 13.

The flow adjusting portion 40 thus configured is disposed in the vicinity of the spouting port 22a, thereby adjusting the flow of the cleaning solution or the like spouted from the spouting port 22a to the route shown in the arrow [G] in FIG. 9, to enable the cleaning solution or the like to always smoothly reach the outer surface of the lateral field-of-view observation window 13.

Fifth Embodiment

Figure 10:
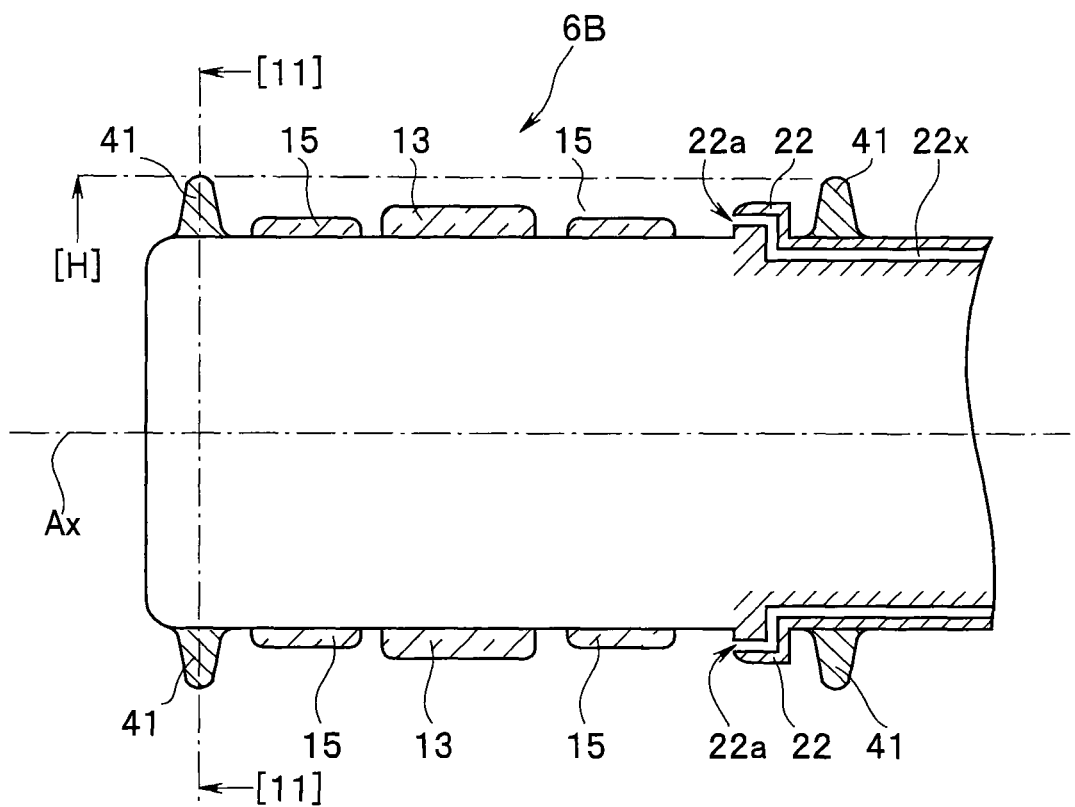
FIG. 10 is a main-part enlarged cross-sectional view illustrating, in an enlarged manner, a distal end portion of an insertion portion of an endoscope according to a fifth embodiment of the present invention.
Figure 11:
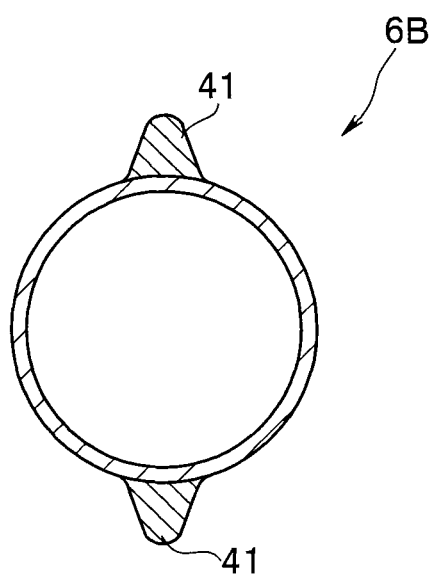
FIG. 11 is a longitudinal cross-sectional view taken along the line [11]-[11] in FIG. 10.

Next, description will be made below on an endoscope according to the fifth embodiment of the present invention. FIGS. 10 and 11 illustrate the endoscope according to the fifth embodiment of the present invention. FIG. 10 is a main-part enlarged cross-sectional view illustrating, in an enlarged manner, a distal end portion of an insertion portion of the endoscope according to the present embodiment. FIG. 11 is a longitudinal cross-sectional view taken along the line [11]-[11] in FIG. 10.

Note that, also in FIGS. 10 and 11, only the constituent parts serving as the gist of the present invention are mainly illustrated similarly as in the above-described first embodiment, and illustration of other constituent members is omitted. That is, in FIGS. 10 and 11, only the constituent members arranged on the circumferential surface (that is, lateral sides) around the longitudinal axis of the distal end portion are illustrated, and illustration of the constituent elements on the front surface is omitted. In FIGS. 10 and 11, the detailed configurations of the internal constituent members of the distal end portion are not directly related to the present invention, so the illustration thereof is omitted. Note that the reference sign Ax denotes the longitudinal axis (also referred to as insertion axis) of the endoscope in FIG. 10.

The basic configuration of the present embodiment is substantially the same as that in the above-described first embodiment. Therefore, the constituent elements same as those in the first embodiment are attached with the same reference signs, and detailed descriptions thereof will be omitted. Only the parts different from the first embodiment will be detailed below.

A distal end portion 6B of the insertion portion of the endoscope according to the present embodiment includes various constituent members (13, 15, 22) provided so as to protrude in the radial direction on the circumferential surface, similarly as in the above-described first embodiment. In addition, in the distal end portion 6B according to the present embodiment, protruding portions 41 which are protrusions formed so as to protrude outward in the radial direction from the circumferential surface of the distal end portion 6B are provided respectively at a portion which is in the vicinity of the distal-end-side lateral field-of-view illumination windows 15 of the pairs of lateral field-of-view illumination windows 15 and which is on the distal end side with respect to the distal-end-side lateral field-of-view illumination windows 15 and at a portion which is in the vicinity of the lateral field-of-view observation window nozzles 22 and which is on the proximal end side with respect to the lateral field-of-view observation window nozzles 22.

In this case, the protruding portions 41 are formed such that the maximum protruding dimensions (see the reference sign [H] in FIG. 10) of the top portions of the protruding portions 41 are "larger" than the maximum protruding dimensions of the any other various constituent members formed on the circumferential surface of the distal end portion 6B so as to protrude in the radial direction, that is, the lateral field-of-view observation windows 13, the lateral field-of-view illumination windows 15, and the lateral field-of-view observation window nozzles 22.

That is, at the distal end portion 6B, the maximum outer diameter dimensions of the portions where the protruding portions 41 (protrusions) are protruded in the radial direction around the longitudinal axis Ax are set to be "larger" than the maximum outer diameter dimension of the portion where the lateral field-of-view observation window nozzles 22 are protruded (or the outer diameter dimension of the portion where the spouting ports 22a are provided). Note that, for example, the round chamfering is applied to the distal end top portions of the protruding portions 41.

In addition, each of the protruding portions 41 is set to be "larger" than the width dimension (dimension in the circumferential direction) of at least the lateral field-of-view observation window nozzle 22.

Furthermore, the height dimension of the protruding portions 41, that is, the maximum outer diameter dimensions (reference sign [H]) of the portions where the top portions are located have to be set so as not to interfere with the illuminating range of the illumination light emitted from the pair of lateral field-of-view illumination windows 15.

Note that the protruding portions 41 have only to be formed so as to be integrated with the distal end portion 6B. Alternatively, for example, the protruding portions 41 may be formed as constituent members separated from the distal end portion 6B, and the protruding portions 41 as the separated members may be fixed to predetermined portions of the distal end portion 6B with various fixing means such as adhesion, screwing, fitting and the like so as to be integrated with the distal end portion 6B. Other configurations are substantially the same as those in the above-described first embodiment.

In the endoscope according to the fifth embodiment thus configured, the protruding portions 41 are formed at the predetermined portions on the circumferential surface of the distal end portion 6B, thereby preventing the various constituent members such as the lateral field-of-view observation window nozzles 22, etc., which are formed so as to protrude from the circumferential surface in the radial direction, from contacting the mucosa on the inner wall of the body cavity, when the insertion/extraction operation or the bending operation of the endoscope is performed in the body cavity of the subject.

In addition, in this case, the round chamfering is applied to the distal end top portions of the protruding portions 41. Therefore, when the insertion/extraction operation or bending operation is performed, with the distal end top portions of the protruding portions 41 contacting the mucosa on the inner wall of the body cavity, the protruding portions 41 smoothly slide on the surface of the mucosa on the inner wall of the body cavity. That is, the smooth insertion/extraction operation or bending operation of the endoscope 2 can be performed in the body cavity.

As described above, according to the fifth embodiment, smooth insertion/extraction operation and bending operation of the endoscope are enabled only by forming the protruding portions 41 at the predetermined portions on the circumferential surface of the distal end portion 6B.

Note that the present embodiment shows the exemplary configuration in which the protruding portions 41 are provided respectively at the portion which is more distal end side with respect to the distal-end-side lateral field-of-view illumination windows 15 and at the portion which is more proximal end side with respect to the lateral field-of-view observation window nozzles 22. However, the present invention is not limited to this example.

As an another exemplary configuration, for example, the protruding portions 41 may be provided in the vicinity of the lateral field-of-view observation window nozzle 22 at only one portion on the distal end side or the proximal end side with respect to the lateral field-of-view observation window nozzles 22. Also such a configuration is capable of providing substantially the same effects as those in the second embodiment.

Sixth Embodiment

As described above, the fifth embodiment shows the example in which the protruding portions 41 are provided such that the maximum outer diameter dimensions of the portions where the protruding portions 41 are protruded are "larger" than the maximum outer diameter dimensions of the any other protruding portions of the constituent members (15, 13, 22) formed on the circumferential of the distal end portion. In addition, the fifth embodiment shows the exemplary configuration in which the protruding portions 41 are respectively provided at the portion on the more distal end side with respect to the distal-end-side lateral field-of-view illumination windows 15 and at the portion on the more proximal end side with respect to the lateral field-of-view observation window nozzles 22, and the exemplary configuration in which the protruding portions 41 are provided in the vicinity of the lateral field-of-view observation window nozzle 22.

The configuration of the protruding portions 41 is not limited to the configuration shown in the fifth embodiment, and various other exemplary configurations can be considered.

Figure 12:
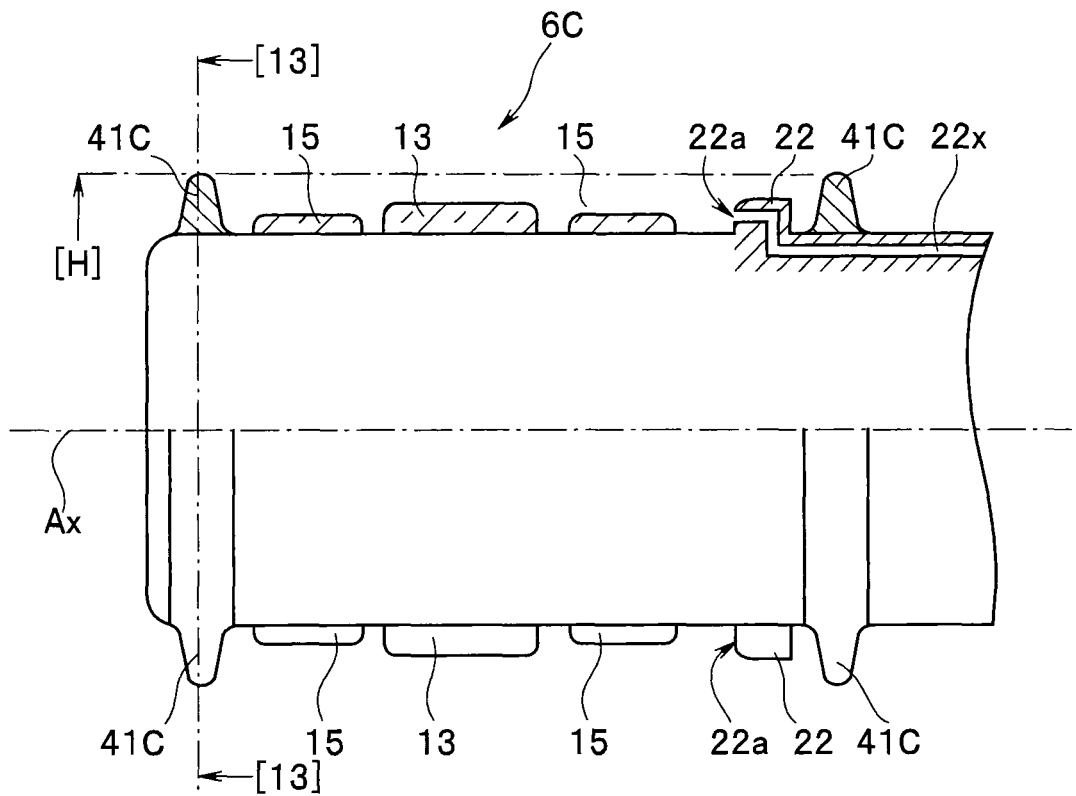
FIG. 12 is a main-part enlarged cross-sectional view illustrating, in an enlarged manner, a distal end portion of an insertion portion of an endoscope according to a sixth embodiment of the present invention.
Figure 13:
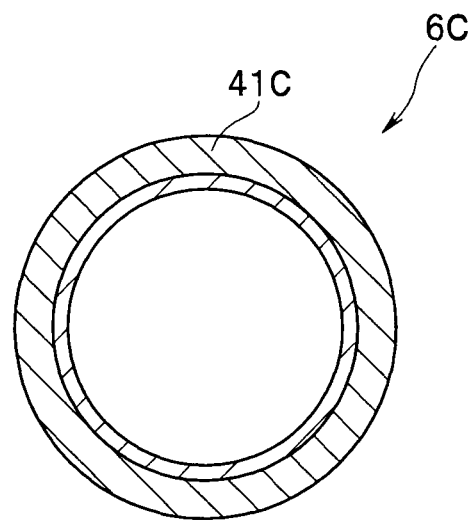
FIG. 13 is a longitudinal cross-sectional view taken along the line [13]-[13] in FIG. 12.

For example, FIGS. 12 and 13 illustrate a distal end portion of an insertion portion of an endoscope according to the sixth embodiment of the present invention. FIG. 12 is a main-part enlarged cross-sectional view illustrating, in an enlarged manner, the distal end portion of the insertion portion of the endoscope according to the present embodiment. FIG. 13 is a longitudinal cross-sectional view taken along the line [13]-[13] in FIG. 12.

Note that, also in FIGS. 12 and 13, the way of description is conformed to the descriptions and illustration forms in the above-described respective embodiments, that is, only the constituent parts serving as a gist of the present invention are illustrated and illustration of other constituent members is omitted, similarly as in the fifth embodiment (FIGS. 10 and 11).

The present embodiment shows an example in which protruding portions 41C protruding outward from the circumferential surface of a distal end portion 6C in the radial direction and formed over the entire circumference in the circumferential direction of the distal end portion 6C are provided.

In the present embodiment, the protruding portions 41C are set such that the maximum outer diameter dimensions (see the reference sign [H] in FIG. 12) of the portions where the protruding portions 41C are formed are "larger" than the maximum outer diameter dimensions of the any other protruding portions of the constituent members (15, 13, 22) provided on the circumferential surface of the distal end portion. The present embodiment shows an exemplary configuration in which the protruding portions 41C are provided respectively at a portion on the more distal end side with respect to the distal-end-side lateral field-of-view illumination windows 15 and at a portion on the more proximal end side with respect to the lateral field-of-view observation window nozzles 22.

That is the protruding portions 41C in the present embodiment are only different from those in the fifth embodiment in that the protruding portions are formed over the entire circumference in the circumferential direction. Other configurations are the same as those in the fifth embodiment.

Also such a configuration is capable of providing the same effects as those in the fifth embodiment. Furthermore, also in the sixth embodiment, the protruding portions 41C may be provided only in the vicinity of the lateral field-of-view observation window nozzles 22, and also in such a case, the same effects can be obtained.

Seventh Embodiment

Figure 14:
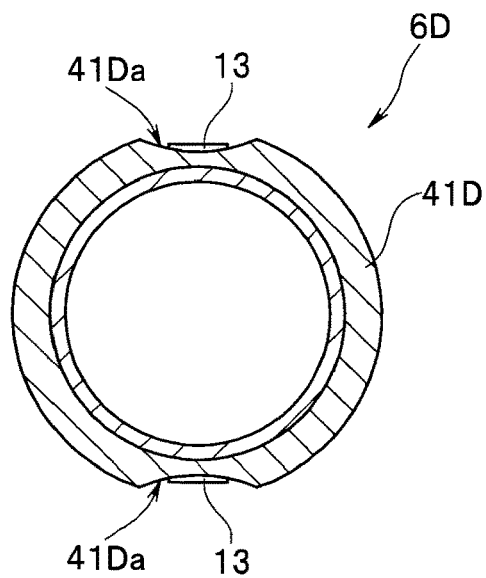
FIG. 14 is a longitudinal cross-sectional view of a surface perpendicular to a longitudinal axis of a distal end portion of an insertion portion of an endoscope according to a seventh embodiment of the present invention.

For example, FIG. 14 illustrates a distal end portion of an insertion portion of an endoscope according to the seventh embodiment of the present invention, and is a longitudinal cross-sectional view of a surface perpendicular to a longitudinal axis of the distal end portion of the insertion portion of the endoscope of the present embodiment.

Note that FIG. 14 illustrates a cross section corresponding to the part along the line [13]-[13] in FIG. 12. FIG. 14 is also conformed to the illustration forms in the above-described respective embodiments.

In the present embodiment, protruding portions 41D are formed on the circumferential surface of a distal end portion 6D over the entire circumference, in substantially the same manner as in the sixth embodiment. In this case, the protruding portions 41D in the present embodiment are configured so as not to shield the illumination range of the illumination light emitted from the pairs of lateral field-of-view illumination windows 15 or the field-of-view range of the lateral field-of-view observation windows 13, for example.

That is, in the seventh embodiment, the protruding portions 41D provided over the entire circumference in the circumferential direction of the distal end portion 6D respectively include cutout portions 41Da which are provided in the vicinity of the portions where the lateral field-of-view illumination windows 15 and the lateral field-of-view observation windows 13 are disposed and which are recessed in the radial direction.

That is, in each of the protruding portions 41D, the height dimension of the part corresponding to the lateral field-of-view illumination windows 15 and the lateral field-of-view observation window 13 (the maximum protruding dimension, the part corresponding to the reference sign [H] in FIG. 12) is set to be "smaller" than the maximum protruding dimension of the other parts.

The cutout portions 41Da formed by cutting a part of the respective protruding portions 41D are provided, thereby capable of preventing the illumination light emitted from the lateral field-of-view illumination windows 15 and the field-of-view range of the lateral field-of-view observation windows 13 from being interfered with. In addition, providing the protruding portions 41D is capable of providing the same effects as those in the fifth embodiment, that is, capable of preventing the constituent members, which are formed on the circumferential surface of the distal end portion 6D so as to protrude in the radial direction, from contacting the mucosa on the inner wall of the body cavity at the time of insertion/extraction operation or bending operation.

Note that it is needless to say that the configuration of the protruding portions 41D of the present embodiment can be applied also to the protruding portions 41 in the fifth embodiment (FIGS. 10 and 11).

Eighth Embodiment

Figure 15:
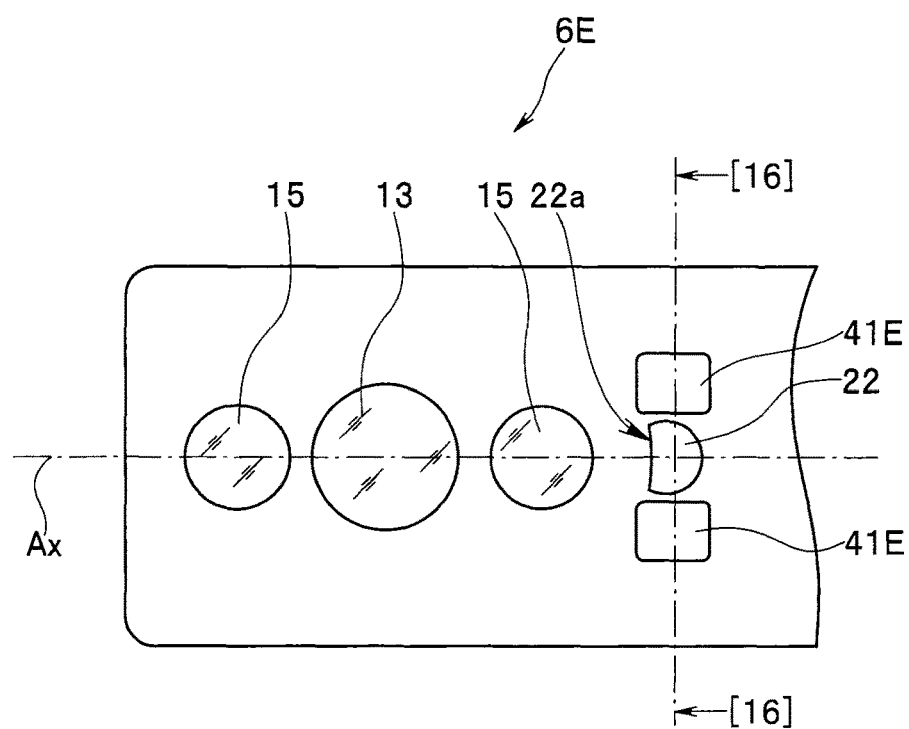
FIG. 15 is a plan view illustrating a side surface of a distal end portion of an insertion portion of an endoscope according to an eighth embodiment of the present invention.
Figure 16:
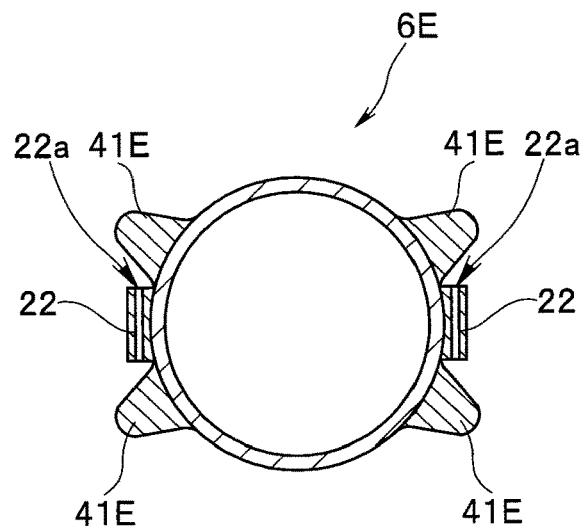
FIG. 16 is a longitudinal cross-sectional view taken along the line [16]-[16] in FIG. 15.

For example, FIGS. 15 and 16 illustrate a distal end portion of an insertion portion of an endoscope according to the eighth embodiment of the present invention. FIG. 15 is a plan view showing the side surface of the distal end portion of the insertion portion of the endoscope according to the present embodiment. FIG. 16 is a longitudinal cross-sectional view taken along the line [16]-[16] in FIG. 15. FIGS. 15 and 16 are also conformed to the illustration forms in the above-described respective embodiments.

In the present embodiment, a pair of protruding portions 41, each of which is formed on the circumferential surface of a distal end portion 6E so as to protrude in the radial direction, are disposed in the vicinity of each of the lateral field-of-view observation nozzles 22 so as to sandwich each of the lateral field-of-view observation window nozzles 22 in the circumferential direction. In this case, the maximum outer diameter dimensions of the portions where the protruding portions 41E are provided are set to be "larger" than the maximum outer diameter dimensions of the any other protruding portions of the constituent members (15, 13, 22) on the circumferential surface of the distal end portion 6E. Other configurations are substantially the same as those in the fifth embodiment. Also such a configuration is capable of providing the same effects as those in the fifth embodiment.

Ninth Embodiment

Figure 17:
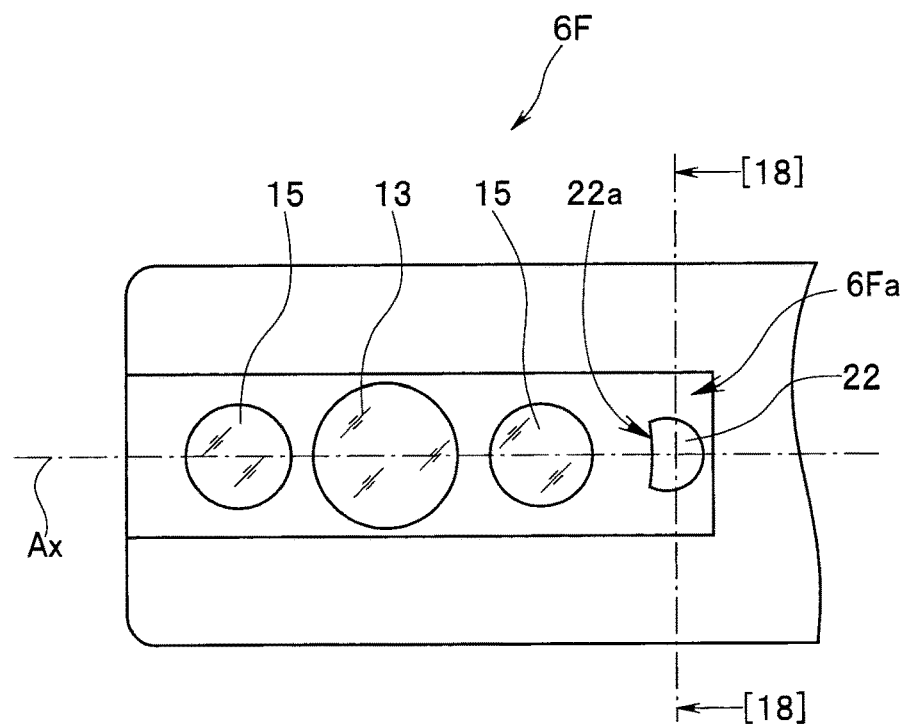
FIG. 17 is a plan view illustrating a side surface of a distal end portion of an insertion portion of an endoscope according to a ninth embodiment of the present invention.
Figure 18:
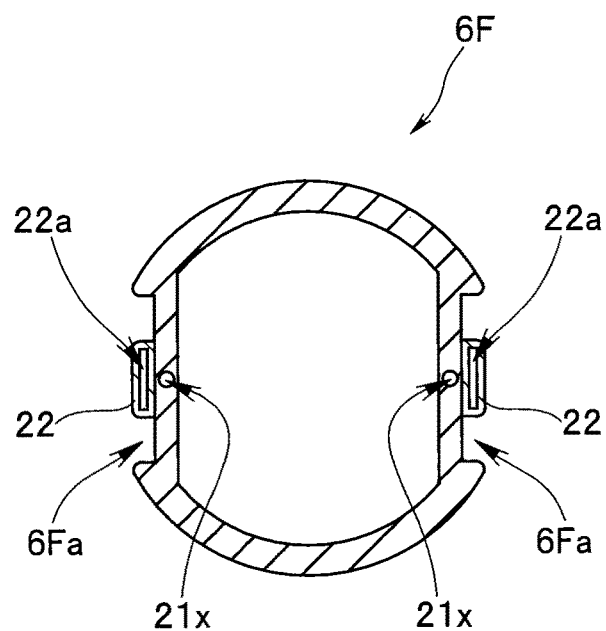
FIG. 18 is a longitudinal cross-sectional view taken along the line [18]-[18] in FIG. 17.

For example, FIGS. 17 and 18 illustrate a distal end portion of an insertion portion of an endoscope according to the ninth embodiment of the present invention. FIG. 17 is a plan view illustrating a side surface of the distal end portion of the insertion portion of the endoscope according to the present embodiment. FIG. 18 is a longitudinal cross-sectional view taken along the line [18]-[18] in FIG. 17. FIGS. 17 and 18 are also conformed to the illustration forms in the above-described respective embodiments.

A distal end portion 6F according to the present embodiment is same as the distal end portions in the respective embodiments in that the pair of lateral field-of-view illumination windows 15, the lateral field-of-view observation window 13, and the lateral field-of-view observation window nozzle 22, which are provided on the circumferential surface so as to protrude in the radial direction, are arranged so as to align in the direction along the longitudinal axis Ax.

In the present embodiment, the portion including the region (see the reference sign 6Fa) where the respective constituent members (15, 13, 22) are disposed is formed so as to have a thin diameter by forming the portion one level lower in the radial direction than the outer circumferential surface of the distal end portion 6F. That is, the respective constituent members (15, 13, 22) are arranged at the portion (thin diameter portion 6Fa) which is a thin diameter part of the distal end portion 6F of the insertion portion 4.

In this case, the outer circumferential surface of the distal end portion 6F has the maximum outer diameter dimension at the distal end portion 6F, and the maximum outer diameter dimensions of the protruding portions of the constituent members (15, 13, 22) are set to be "smaller" than the maximum outer diameter dimension of the distal end portion 6F.

With such a configuration, the constituent portion itself of the distal end portion 6F is arranged so as to surround the portion (thin diameter portion 6Fa) where the constituent members (15, 13, 22) are disposed, in the present embodiment. Therefore, in the present embodiment, the constituent portion of the distal end portion 6F has a function corresponding to the protruding portions shown in the respective fifth to eighth embodiments. Other configurations are substantially the same as those in the second embodiment. Also such a configuration is capable of providing the same effects as those in the fifth embodiment.

Tenth Embodiment

Figure 19:
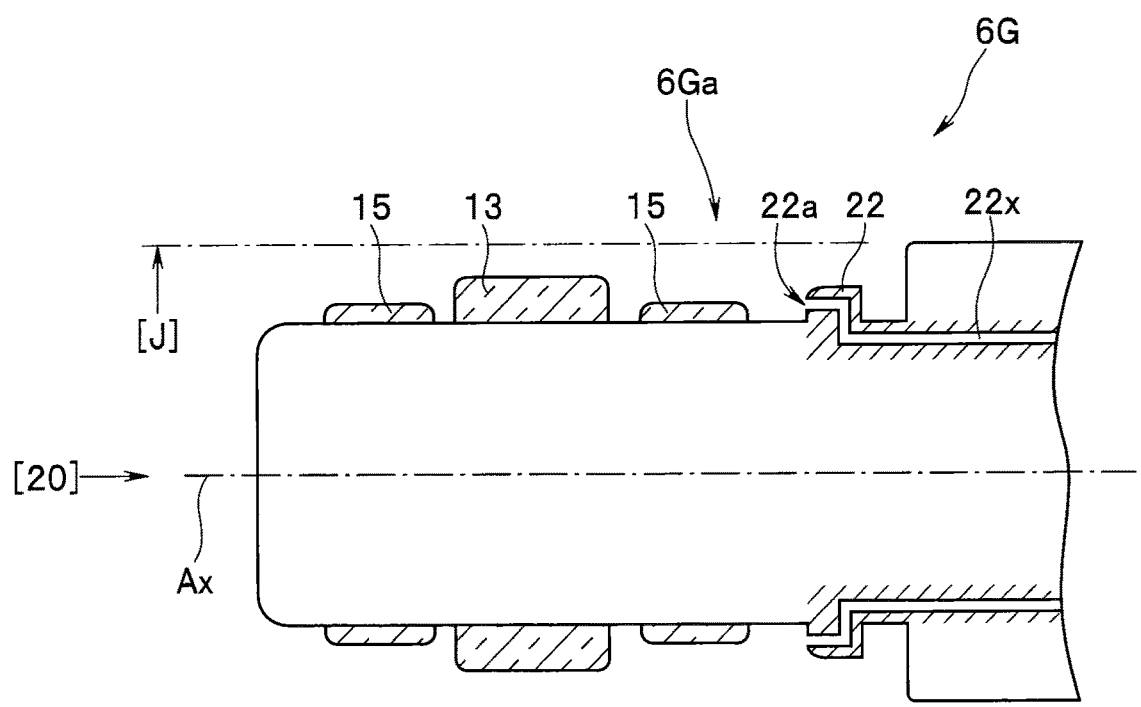
FIG. 19 is a main-part enlarged cross-sectional view illustrating, in an enlarged manner, a distal end portion of an insertion portion of an endoscope according to a tenth embodiment of the present invention.
Figure 20:
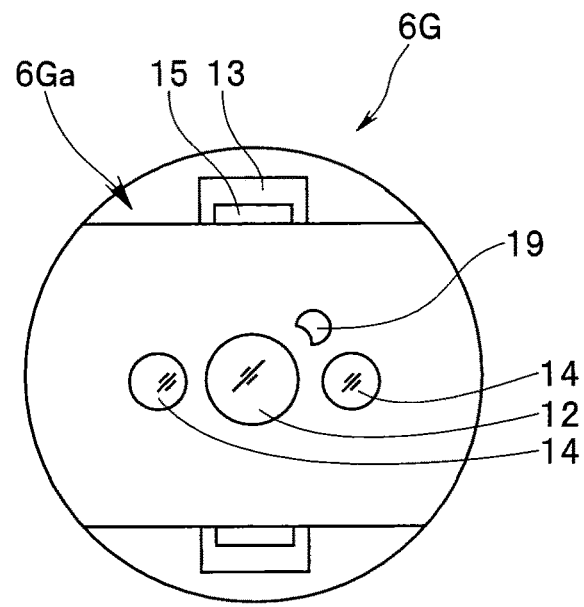
FIG. 20 is a front view of the distal end portion viewed from the direction of the arrow 20 in FIG. 19.

Next, description will be made below on an endoscope according to the tenth embodiment of the present invention. FIGS. 19 and 20 illustrate an endoscope according to the tenth embodiment of the present invention. FIG. 19 is a main-part enlarged cross-sectional view illustrating, in an enlarged manner, the distal end portion of the insertion portion of the endoscope according to the present embodiment. FIG. 20 is a front view of the distal end portion viewed from the direction of the arrow 20 in FIG. 19. Note that FIGS. 19 and 20 are also conformed to the illustration forms in the above-described respective embodiments.

The basic configuration of the present embodiment is substantially the same as that in the first embodiment. Therefore, the constituent elements same as those in the first embodiment are attached with the same reference signs, and detailed descriptions thereof will be omitted. Only the parts different from the first embodiment will be detailed below.

A distal end portion 6G of the insertion portion of the endoscope according to the present embodiment is same as the distal end portions in the respective embodiments in that the pair of lateral field-of-view illumination windows 15, the lateral field-of-view observation window 13, and the lateral field-of-view observation window nozzle 22, which are provided on the circumferential surface so as to protrude in the radial direction, are arranged so as to align in the direction along the longitudinal axis Ax.

The present embodiment is different from the above-described embodiments in that a pair of cutout portions 6Ga formed by cutting a part of the region of the distal end portion 6G are provided, and the constituent members (15, 13, 22) are disposed on the plane portion of each of the cutout portions 6Ga.

In other words, the cutout portions 6Ga formed by cutting a part of the distal end side of the distal end portion 6G are formed one level lower in the radial direction than the outer circumferential surface of the distal end portion 6G so as to form a thin diameter portion, similarly as in the ninth embodiment. That is, the constituent members (15, 13, 22) are arranged in each of the cutout portions 6Ga which form the thin diameter part of the distal end portion 6G of the insertion portion 4.

Also in this case, the outer circumferential surface of the distal end portion 6G has the maximum outer diameter dimension (see the reference sign [J] in FIG. 19) at the distal end portion 6G. The maximum outer diameter dimensions of the protruding portions of the constituent members (15, 13, 22) are set to be "smaller" than the maximum outer diameter dimension (reference sign [J]) of the distal end portion 6G. Other configurations are substantially the same as those in the first embodiment.

The tenth embodiment thus configured is also capable of providing the same effects as those in the first embodiment.

Eleventh Embodiment

Figure 21:
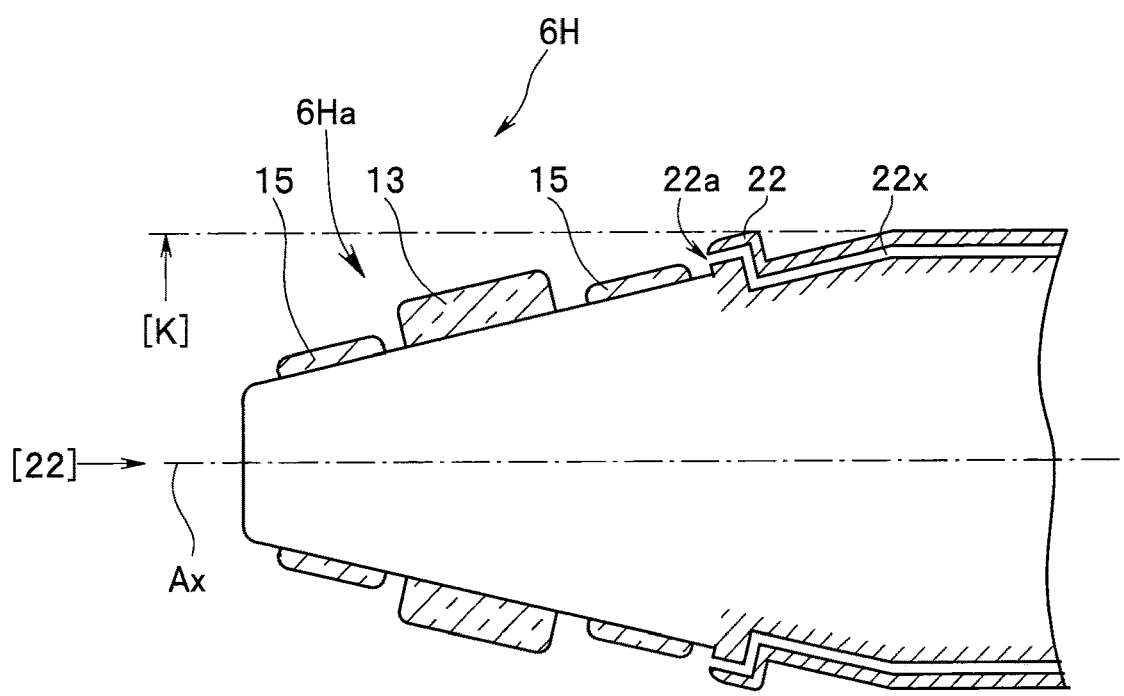
FIG. 21 is a main-part enlarged cross-sectional view illustrating, in an enlarged manner, a distal end portion of an insertion portion of an endoscope according to an eleventh embodiment of the present invention.
Figure 22:
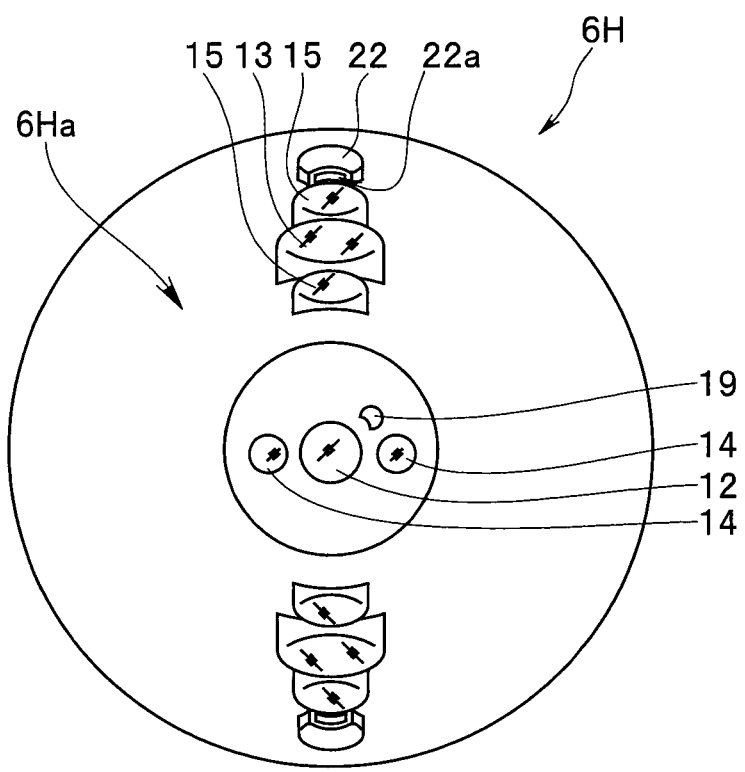
FIG. 22 is a front view of the distal end portion viewed from the direction of the arrow 22 in FIG. 21.

Next, description will be made below on an endoscope according to the eleventh embodiment of the present invention. FIGS. 21 and 22 illustrate an endoscope according to the eleventh embodiment of the present invention. FIG. 21 is a main-part enlarged cross-sectional view illustrating, in an enlarged manner, the distal end portion of the insertion portion of the endoscope according to the present embodiment. FIG. 22 is a front view of the distal end portion viewed from the direction of the arrow 22 in FIG. 21. Note that FIGS. 21 and 22 are also conformed to the illustration forms in the above-described respective embodiments.

The basic configuration of the present embodiment is substantially the same as that in the above-described first embodiment. Therefore, the constituent elements same as those in the first embodiment are attached with the same reference signs, and detailed descriptions thereof will be omitted. Only the parts different from the first embodiment will be detailed below.

A distal end portion 6H of the insertion portion of the endoscope according to the present embodiment is different from the one in the first embodiment in that the distal end portion 6H includes inclined surfaces 6Ha, which form a thin diameter portion, such that the outer circumferential surface of a region on the distal end side is formed to be substantially a conical shape tapered toward the distal end. On the circumferential surface of the tapered inclined region, the pair of lateral field-of-view illumination windows 15, the lateral field-of-view observation window 13, and the lateral field-of-view observation window nozzle 22 are arranged aligned in a row in the direction of the longitudinal axis Ax along each of the inclined surfaces 6Ha having a predetermined inclination angle with respect to the longitudinal axis Ax. That is, the constituent members (15, 13, 22) are arranged on each of the inclined surface 6Ha which is a thin diameter part of the distal end portion 6H of the insertion portion 4.

In this case, the maximum outer diameter dimensions of the portions where the constituent members (15, 13, 22) are provided so as to protrude in the radial direction from the inclined surface 6Ha of the distal end portion 6H are set to be "smaller" than the maximum outer diameter dimension (the reference sign [K] in FIG. 21) of the distal end portion 6H. Other configurations are the same as those in the first embodiment.

The eleventh embodiment thus configured is also capable of providing the same effects as those in the first embodiment.

Twelfth Embodiment

Figure 23:
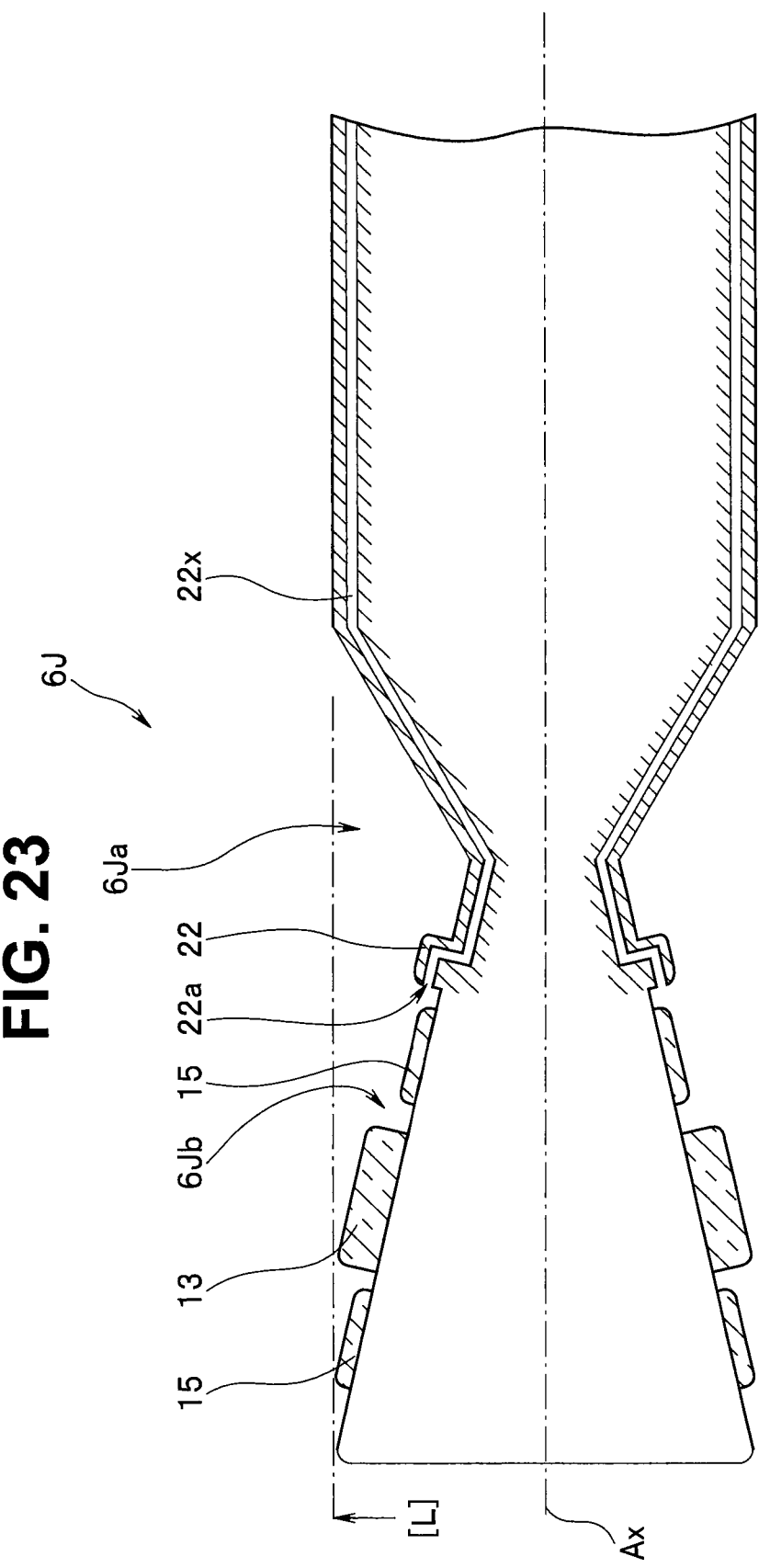
FIG. 23 is a main-part enlarged cross-sectional view illustrating, in an enlarged manner, a distal end portion of an insertion portion of an endoscope according to a twelfth embodiment of the present invention.

Next, an endoscope according to the twelfth embodiment of the present invention will be described below. FIG. 23 is a main-part enlarged cross-sectional view illustrating, in an enlarged manner, the distal end portion of the insertion portion of the endoscope according to the twelfth embodiment of the present invention. Note that FIG. 23 is also conformed to the illustration forms in the above-described respective embodiments. In addition, FIG. 23 illustrates the shape of the distal end portion exaggeratingly so as to clearly describe the gist of the present embodiment.

The basic configuration of the present embodiment is substantially the same as that in the first embodiment. Therefore, the constituent elements same as those in the first embodiment are attached with the same reference signs, and detailed descriptions thereof will be omitted. Only the parts different from the first embodiment will be detailed below.

A distal end portion 6J of the insertion portion of the endoscope according to the present embodiment includes recessed regions 6Ja which form a thin diameter part such that the middle region of the distal end portion 6J is recessed in the radial direction. The recessed regions 6Ja are formed, as shown in the cross section thereof in FIG. 23, by including inclined surfaces 6Jb which are formed in a substantially conical shape so as to be thinner in a tapered manner from the distal end region toward the proximal end side and have a predetermined inclination angle with respect to the longitudinal axis Ax.

On the circumferential surface of the inclined surface 6Jb of each of the recessed regions 6Ja, the pair of lateral field-of-view illumination windows 15, the lateral field-of-view observation window 13, and the lateral field-of-view observation window nozzle 22 are aligned in a row along the inclined surface 6Jb in the direction of the longitudinal axis Ax. That is, the constituent members (15, 13, 22) are arranged on the inclined surface 6Jb which is a thin diameter part of the distal end portion 6J of the insertion portion 4.

In this case, the maximum protruding dimensions of the portions where constituent members (15, 13, 22) are provided so as to protrude in the radial direction from the inclined surface 6Jb of each of the recessed regions 6Ja of the distal end portion 6J are set to be "smaller" than the maximum protruding dimension (the reference sign [L] in FIG. 23) of the distal end portion 6J, as shown in FIG. 23. Other configurations are the same as those in the first embodiment.

The twelfth embodiment thus configured is also capable of providing the same effects as those in the first embodiment.

Thirteenth Embodiment

Figure 24:
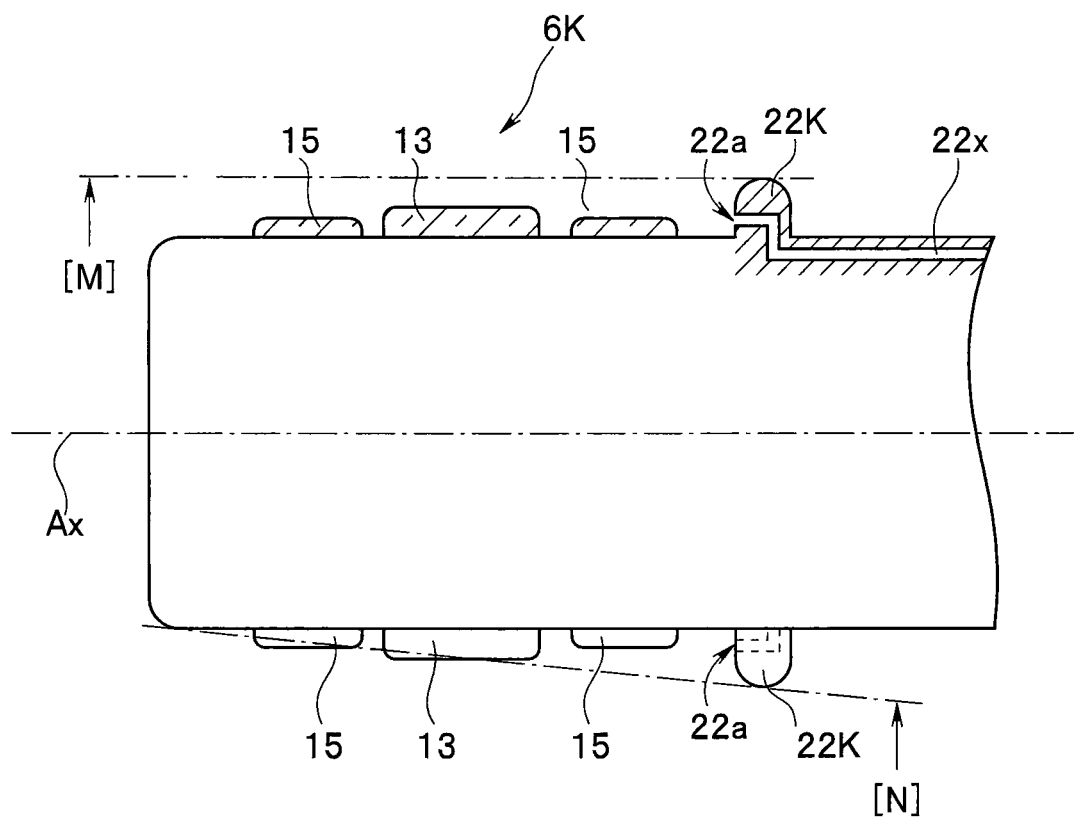
FIG. 24 is a main-part enlarged cross-sectional view illustrating, in an enlarged manner, a distal end portion of an insertion portion of an endoscope according to a thirteenth embodiment of the present invention.

Next, description will be made below on an endoscope according to the thirteenth embodiment of the present invention. FIG. 24 is a main-part enlarged cross-sectional view illustrating, in an enlarged manner, the distal end portion of the insertion portion of the endoscope according to the thirteenth embodiment of the present invention. Note that FIG. 24 is also conformed to the illustration forms in the above-described respective embodiments.

The basic configuration of the present embodiment is substantially the same as that in the above-described first embodiment. Therefore, the constituent elements same as those in the first embodiment are attached with the same reference signs, and detailed descriptions thereof will be omitted. Only the parts different from the first embodiment will be detailed below.

A distal end portion 6K of the insertion portion of the endoscope according to the present embodiment includes a lateral field-of-view observation window nozzle 22K formed by applying round chamfering and the like to the edge portions on the outer surface of the lateral-field-of-view observation window nozzle, similarly as in the third embodiment, and the top portion of the nozzle is formed so as to protrude, as shown in FIG. 24.

In the present embodiment, the top portion of the lateral field-of-view observation window nozzle 22K has the maximum protruding dimension (see the reference sign [M] in FIG. 24) in the radial direction around the longitudinal axis Ax and the maximum protruding dimension of the spouting port 22a in the radial direction is set to be shorter than the maximum protruding dimension (see the reference sign [M]) of the top portion of the nozzle 22K protruded in the radial direction around the longitudinal axis Ax.

Note that, in such a configuration, the spouting port 22a may have a structure for spouting the cleaning solution or the like diagonally toward the direction of the longitudinal axis Ax, that is, the direction of the lateral field-of-view observation window 13.

In addition, in the present embodiment, the position in the radial direction of the spouting port 22a of the lateral field-of-view observation window nozzle 22K may be located within a range smaller in the radial direction than the line (one-dot chain line [N] in FIG. 24) connecting the top portion of the nozzle 22K and the maximum protruding part in the radial direction of the distal-most portion of the distal end portion 6K.

The thirteenth embodiment thus configured is also capable of providing the same effects as those in the first embodiment.

Note that it is needless to say that the present invention is not limited to the above-described embodiments, and various modifications and applications are possible within a range without departing from the gist of the invention. Furthermore, the above-described embodiments include inventions at various stages, and by appropriately combining a plurality of constituent features disclosed in the embodiments, inventions at various stages can also be extracted. For example, even if some constituent features are deleted from all the constituent features shown in the above-described present embodiments, if the problem to be solved by the invention can be solved and the effects of the invention can be obtained, the configuration in which some constituent features are deleted can be extracted as an invention. In addition, the constituent elements in different embodiments may be appropriately combined. The present invention is not limited by the specific embodiments of it except as limited by the appended claims.

The present invention can be applied not only to endoscope control apparatuses in medical fields but also to endoscope control apparatuses in industrial fields.

What is claimed is:

1. An endoscope comprising:
an insertion portion configured to be inserted into an inside of a subject, the insertion portion having a distal end portion disposed on a distal end side of the insertion portion in a direction of a longitudinal axis of the insertion portion;
a pair of first observation image acquiring windows provided on a circumferential surface around the longitudinal axis of the distal end portion, each of the pair of first observation image acquiring windows acquiring a first observation image from a first region of the subject;
a second observation image acquiring window provided on a front surface of the distal end portion, the second observation image acquiring window acquiring a second observation image from a second region of the subject which is different from the first region;

a pair of nozzles, each of the pair of nozzles being provided so as to protrude from the circumferential surface of the distal end portion in a radial direction of the distal end portion, each of the pair of nozzles including a spouting port configured to spout fluid in a direction along the longitudinal axis toward a respective one of the pair of first observation image acquiring windows;

a pair of first protruding portions, each of the pair of first protruding portions being provided so as to protrude from the circumferential surface of the distal end portion in the radial direction of the distal end portion, the pair of first protruding portions being located at a position closer to the front surface of the distal end portion with respect to the pair of first observation image acquiring windows and the pair of nozzles, a maximum dimension in the radial direction of each of the first protruding portions being larger than a dimension in the radial direction of each of the nozzles; and a pair of second protruding portions, each of the pair of second protruding portions being provided so as to protrude from the circumferential surface of the distal end portion in the radial direction of the distal end portion, the pair of second protruding portions being located at a position farther from the front surface of the distal end portion with respect to the pair of first observation image acquiring windows and the pair of nozzles, a maximum dimension in the radial direction of each of the second protruding portions being larger than the dimension in the radial direction of each of the nozzles.

2. The endoscope according to claim 1, further comprising two pairs of illumination windows that illuminate a predetermined region of the subject, each pair of the two pairs of illumination windows being provided on the circumferential surface of the distal end portion along the longitudinal axis direction so as to sandwich each of the pair of first observation image acquiring windows therebetween.

3. The endoscope according to claim 2, wherein, the circumferential surface of the distal end portion includes in a following alignment order from a distal end side in the longitudinal axis direction of the insertion portion:

one of the pair of the first protruding portions; one of the one pair of illumination windows;

one of the pair of the first observation image acquiring windows; another of the one pair of illumination windows;

one of the pair of nozzles; and one of the pair of the second protruding portions.

4. The endoscope according to claim 2, wherein the spouting port is provided in a dimension range smaller than a maximum dimension in the radial direction of the illumination portions protruding in the radial direction of the distal end portion.

5. The endoscope according to claim 1, wherein the pair of the first observation image acquiring windows, the pair of nozzles, the pair of the first protruding portions, and the pair of the second protruding portions are respectively provided at positions across the longitudinal axis.

6. The endoscope according to claim 1, wherein a part of the distal end portion is formed to have a diameter thinner than proximal portions of the insertion portion.

7. The endoscope according to claim 6, wherein each of the nozzles is arranged in a thin diameter part of the distal end portion of the insertion portion.

8. The endoscope according to claim 1, wherein each of the pair of first observation image acquiring windows includes a first image pickup section that photoelectrically converts the first observation image, and the second observation image acquiring window includes a second image pickup section that photoelectrically converts the second observation image, the second image pickup section being different from the first image pickup section.

* * * * *